(12) United States Patent
Petit et al.

(10) Patent No.: US 6,548,475 B1
(45) Date of Patent: *Apr. 15, 2003

(54) USE OF THE KAL PROTEIN AND TREATMENT WITH THE KAL PROTEIN IN TREATMENT OF RETINAL, RENAL, NEURONAL AND NEURAL INJURY

(75) Inventors: Christine Petit, Le Plessis-Robinson (FR); Nadia Soussi-Yanticostas, Paris (FR); Jean-Pierre Hardelin, Paris (FR); Catherine Sarailh, Marseille (FR); Genevieve Rougon, Marseille (FR); Renaud Legouis, Strasbourg (FR); Olivier Ardouin, Issy-les-Mou-lineaux (FR); Jean-Claude Mazie, Asnieres (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/576,967

(22) Filed: May 24, 2000

Related U.S. Application Data

(62) Division of application No. 08/761,136, filed on Dec. 6, 1996, now Pat. No. 6,121,231.

(51) Int. Cl.$^7$ .......................... A01N 37/18; A61K 38/00
(52) U.S. Cl. ............................... 514/2; 514/8; 514/12; 530/300; 530/350
(58) Field of Search ................... 514/2, 8, 12; 530/300, 530/350

(56) References Cited

U.S. PATENT DOCUMENTS 6,121,231 A * 9/2000 Petit et al. ..................... 514/2

OTHER PUBLICATIONS

Legouis et al., Cell, 67, pp. 423–435, 1991.*

Buttiglione et al., "F3 Neuronal Adhesion Molecule Controls Outgrowth and Fasciculation of Cerebellar Granule Cell Neurites: A Cell–Type–Specific Effect Mediated by the Ig–Like Domains", Molecular and Cellular Neuroscience 000, pp. 1–17, (1996).

Chang et al., "Extension of Neurites on Axons is Impaired by Antibodies Against Specific Neural Cell Surface Glycoproteins", The Journal of Cell Biology, vol. 104, pp. 355–362, Feb. 1987.

Castillo et al., "Structure of the X–Linked Kallmann Syndrome Gene and Its Homologous Pseudogene on the Y Chromosome", Nature Genetics, vol. 2, pp. 305–310, Dec. 1992.

Kunz et al., Intracellular Signaling is Changed After Clustering of the Neural Cell Adhesion Molecules Axonin–1 and NgCAM During Neurite Fasciculation, The Journal of Cell Biology, vol. 135, No. 1, pp. 253–266, Oct. 1996.

Soussi–Yanicostas et al., "Initial Characterization of Anosmin–1, A Putative Extracellular Matrix Protein Synthsized By Definite Neuronal Cell Populations In The Central Nervous System", Journal of Cell Science 109, 1749–1757, (1996).

Rapp, L.M. in Handbook of Neurotoxicology, Chang et al ets., Marcel Dekker Inc., 1995 pp. 963–1003.

Sambrook et al. Molecular Cloning A Laboratory Manual, Second Edition, vol. 3, pp 16.1–16.80, Cold Spring Harbor Press, 1989.

Jackowski, et al., British Journal of Neurosurgery, 9:303–317, 1995.

Barinaga, M., Science, 264:772–774, 1994.

Del Castillo, et al., Methods in Molecular and Cellular Biology, 4:87–92, 1993.

Legouis, et al., Cell, 67:423–435, 1991.

* cited by examiner

*Primary Examiner*—John Ulm
*Assistant Examiner*—Olga N. Chernyshev
(74) *Attorney, Agent, or Firm*—Oblon, Spivak, McClelland, Maier & Neustadt, P.C.

(57) ABSTRACT

KAL protein is identified as the active agent in a therapeutic composition for treatment of injury to nerve tissue, including spinal cord tissue, as well as support of treatment for renal grafts. Additionally, therapeutic treatment of renal injury, and kidney transplantation and renal surgery, is effected by administration of KAL protein. The therapeutic agent may be administered locally, or intravenously. Retinal disorders may be similarly treated.

5 Claims, 17 Drawing Sheets

USE OF THE KAL PROTEIN AND TREATMENT WITH THE KAL PROTEIN IN TREATMENT OF RETINAL, RENAL, NEURONAL AND NEURAL INJURY

This application is a Division (CIP) of application Ser. No. 08/761,136 Filed on Dec. 6, 1996, now U.S. Pat. No. 6,121,231.

BACKGROUND OF THE INVENTION

1. Field of the Invention

This invention pertains to the use of the KAL protein and to the treatment of patients suffering from neural, retinal and renal insult.

2. Background of the Invention

Kallmann's syndrome (KS) refers to the association of hypogonadism with anosmia (or hyposmia). Hypogonadism in KS is due to gonadotropin-releasing hormone (GnRH) deficiency (Naftolin et al., 1971; Sherins and Howards, 1986). Anosmia has been related to the absence or hypoplasia of the olfactory bulbs and olfactory tracts (De Morsier, 1954). In animals, the existence of interactions between olfactory and reproductive functions has long been reported (Whitten, 1956 Bruce, 1959; McClintock, 1971). More recently, developmental links between the olfactory system and the GnRH neuroendocrine system have also been identified. Embryo logical studies in several species including mouse (Schwanzel-Fukuda and Pfaff, 1989; Wray et al., 1989), monkey (Ronnekleiv and Resko, 1990), chicken (Murakami et al., 1991; Norgren and Lehman, 1991 Nurakami and Akai, 1996), newt (Murakami et al., 1992) and man (Schwanzel-Fukuda et al., 1995), have led to the conclusion that GnRH synthesizing neurons migrate from the olfactory epithelium to the brain during embryonic life. GnRH cells migrate along an olfactory epithelium-forebrain axis of nerve fibers. In mammals, migrating GnRH cells are primarily found in close association with the vomeronasal and terminal nerves (Schwanzel-Fukuda et al, 1992), whereas in the chicken they appear to ascend along the olfactory nerves themselves (Murakami et al., 1991). Ultimately, the GnRH neurons reach the preoptic and hypothalamic areas where the neurosecretion takes place. From these observations, it was first hypothesized that the "double clinical defect" observed in KS affected patients (i.e. hypogonadism and anosmia) could be related to a unique defect in the development process of both olfactory and GnRH neurons.

The study of a human 19 week old male fetus carrying a large Xp deletion, including the KAL gene responsible for the X-linked form of the disease, has shown that neither the GnRH neurons, nor the axon terminals of the olfactory, terminalis and vomeronasal neurons were present in the brain. Although GnRH cells and olfactory axons had left the olfactory epithelium, they had accumulated in the upper nasal area, on the peripheral side of the dura layer (Schwanzel-Fukuda et al., 1989). This observation indicated that the embryonic defect responsible for the X-linked KS did not involve the initial differentiation step of olfactory and GnRH neurons within the olfactory placode, but rather the subsequent migration pathway of olfactory axons and GnRH cells to the brain. Furthermore, some patients have unilateral renal aplasia (Wegenke et al., 1975).

The human KAL gene has been isolated by positional cloning strategies (Franco et al., 1991; Legouis et al., 1991; Hardelin et al., 1992). The gene encodes a 680 amino acid putative protein (SwissProt P23352) including a signal peptide. The deduced amino acid sequence provides no evidence for either a hydrophobic transmembrane domain or glycosyl phosphatidyl inositol anchorage, suggesting that the protein is extracellular.

The interspecies conservation of the KAL gene sequence has been explored by Southern blot analysis with human KAL cDNA probes. Cross hybridization was observed in various mammals and in the chicken (Legouis et al., 1993). The KAL orthologue has been isolated in the chicken (Legouis et al., 1993; Rugarli et al., 1993). Sequence comparison with the human KAL cDNA demonstrated an overall identity of 72%, with 75% identity at the protein level.

The expression of the KAL gene during embryonic development has been studied in the chicken by in situ hybridization (Legouis et al., 1993; Legouis et al., 1994; Rugarli et al., 1993). From embryonic day 2 (ED2) to ED8, the KAL gene is expressed in various endodermal, mesodermal and ectodermal derivatives, whereas from ED8 onwards, the expression is almost entirely restricted to definite neuronal populations in the central nervous system including mitral cells in the olfactory bulbs, Purkinje cells in the cerebellum, striatal, retinal and tectal neurons, most of which still express the gene after hatching. According to such a spatiotemporal pattern of expression, it is proposed that the KAL gene is involved both in morphogenetic events and in neuronal late differentiation and/or survival.

SUMMARY OF THE INVENTION

There is no adequate treatment presently available that leads to specific growth and guidance of neurons which have been injured or have degenerated.

Surprisingly, the inventors have discovered that the purified KAL protein possess different in vitro biological activities including neuron growth activity, and neurite fasciculation activity as well as adhesion properties to cerebellar neurons the latter being mediated, at least in part, via the fibronectin type III of the KAL protein.

In addition the KAL protein is an appropriate substrate for neuronal survival. Given these properties, the KAL protein, its receptor(s) and its ligands are relevant to neuronal regeneration:

survival adhesion growth fasciculation

Consequently, an object of the present invention concerns the therapeutic use of KAL protein or one of its biologically active derivatives, alone or in combination with other ligands, in disease of central or peripheral nervous system including:

One subject of the present invention is a therapeutic composition comprising a pharmaceutically active amount of a protein selected among the group consisting of:

the purified KAL protein;

a protein having at least 80% homology in amino acid sequence with the KAL protein; or with protein having at least 80% homology in aminoacid sequence with a purified biologically active part of the KAL protein;

a protein which is specifically recognized by antibodies directed against the purified KAL protein.

By "bologically active part" of the KAL protein is intended a peptide having an aminoacid sequence which is contained in the entire aminoacid sequence of the KAL protein and which peptide exhibits at least one of the following in vitro activities survival activity for cells, and specifically for neurons;

Growth promoting activity for neurons;

induction of neurite fasciculation;

Adhesion function.

A particular biologically active part of the KAL protein consists in one or several of the four fibronectin type III repeat of the KAL protein (FIG. 9) alone or in combination one with each other that are obtained by transfection of a procaryotic or an eukaryotic cell, specifically a CHO cell with the corresponding encoding DNA that has been inserted in a suitable expression vector.

Thus, this therapeutic composition according to the present invention comprises either the KAL protein or one of its "biologically active derivatives" that are above defined.

Another subject of the present invention is a therapeutic composition containing a pharmaceutically effective amount of a polynucleotide sequence (RNA, genomic DNA or cDNA) coding for the purified KAL protein or a biologically active derivative of the KAL protein.

Another subject of the present invention is a method for cultivating neuronal cells in vitro comprising the addition of a biologically active amount of either the purified KAL protein, a protein having at least 80% homology in aminoacid sequence with the KAL protein or a purified biologically active part of the KAL protein to the cell culture medium.

Another subject of the present invention is a method for the production of the purified recombinant KAL protein comprising the steps of:

a) Cultivating a prokaryotic or an eukaryotic cell that has been transfected with a vector carrying a DNA insert coding for the KAL protein, a purified biologically active part of the KAL protein or a protein which is recognized by antibodies directed against the purified KAL protein a purified biologically active part of the KAL protein or a protein which is recognized by antibodies directed against the purified KAL protein b) isolating the recombinant KAL protein from the culture preparation of the transfected prokaryotic and eukaryotic cell.

Another subject of the present invention is a method for screening ligands that binds to the KAL protein.

Another subject of the present invention is a method for screening molecules that modulates the expression of the KAL protein.

1. Nerve injury of traumatic, infectious, metabolic or inherited origin.
2. Spinal injury of traumatic, infectious, metabolic or inherited origin.
3. Retinal disorder graft in context of traumatic, infectious, metabolic or inherited origin.

Renal treatment based on the role of the KAL protein in kidney morphogenesis:

4. Renal disease, hypoplasia or agenesis of traumatic, infectious, metabolic or inherited origin.
5. Kidney transplantation and renal surgery.

The diseases giving rise to these conditions are varied and include, among others, amyotrophic lateral sclerosis, multiple sclerosis, Parkinson's, injuries of traumatic origin, neurotrophic ulcers, macular degeneration, diabetes, leprosy and renal failure.

The clinical use of the KAL protein can be administered in the form of a solution, gel or dry powder. It can be introduced locally. It can be administered intraveneously using devices that overcome the blood brain barrier.

The results are expressed as the percentage of adherent cells, relative to the total number of cells deposited in the well.

Figure 2:
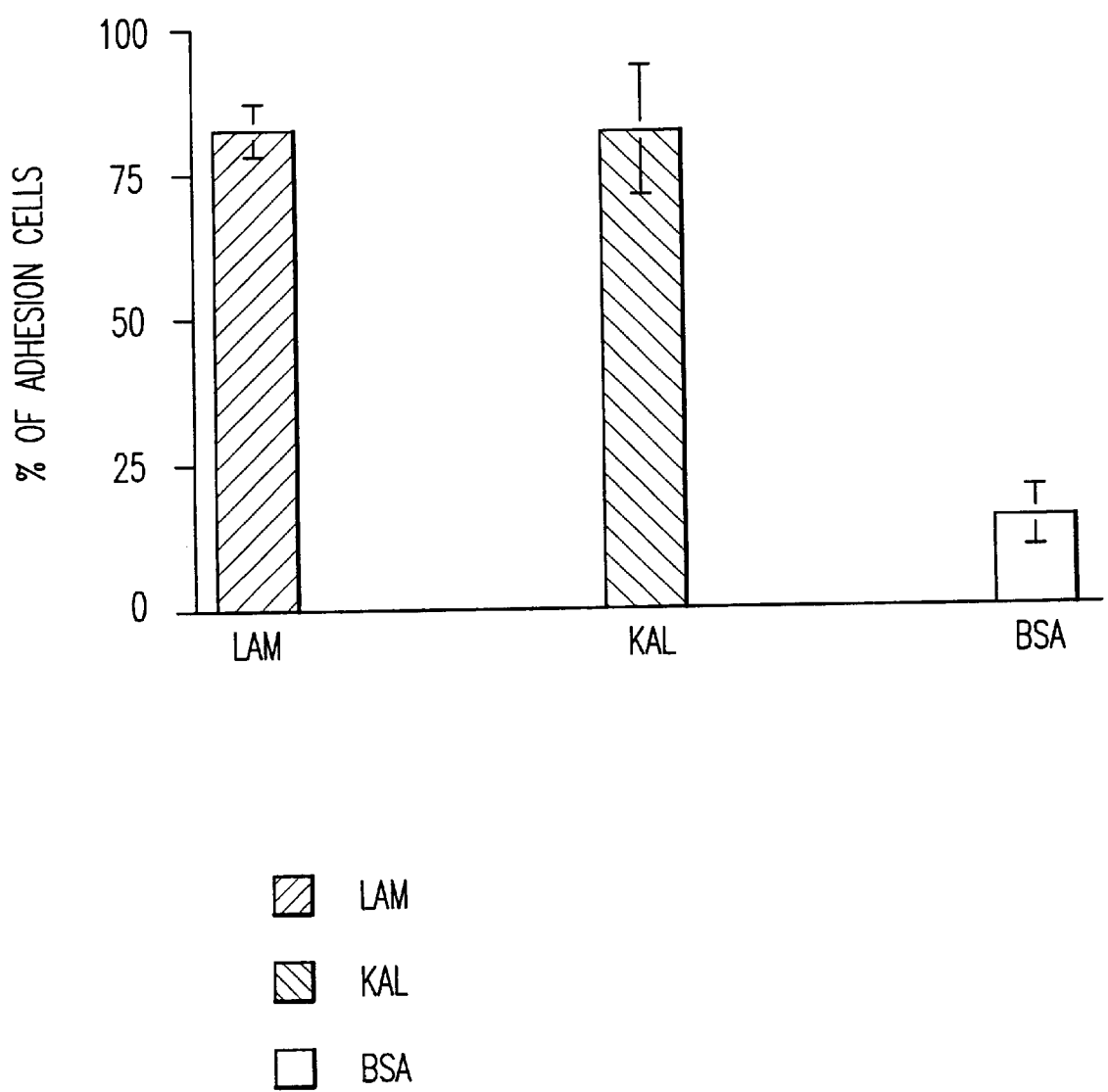

FIG. 2. The KAL protein promotes the adhesion of PC12 cells. PC12 cells were plated on plastic surfaces which were coated with KAL protein, or with BSA, or with laminin for 90 min at 37° C. as described in materials and methods. The wells were washed three times with PBS and adherent cells were counted as described in Materials and Methods.

The results are expressed as the percentage of adherent cells, in relation to the total number of cells deposited on the substratum.

Figure 3:
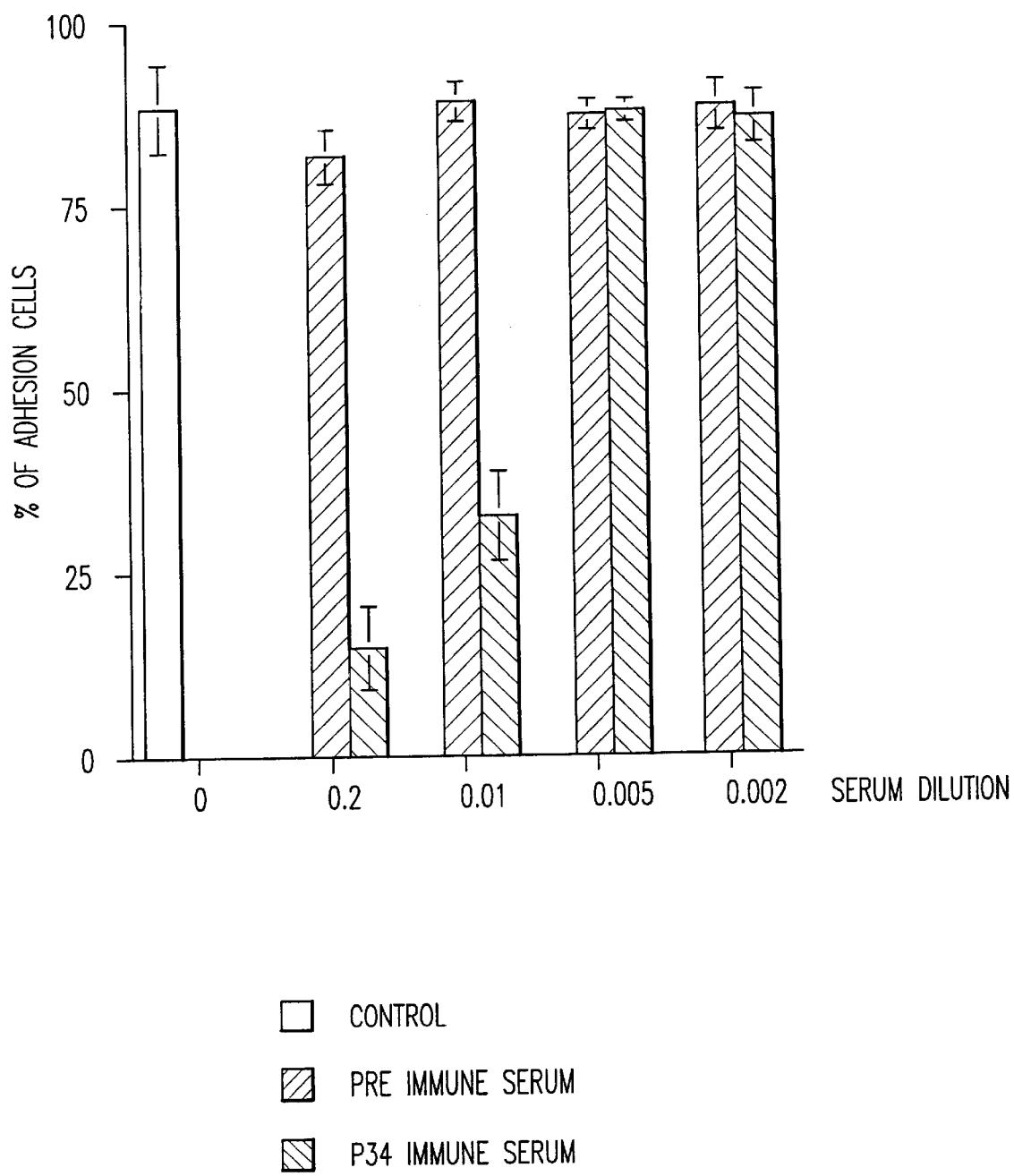

FIG. 3. Antibody-mediated inhibition of PC12 cell adhesion to the KAL protein. PC12 cells were plated on wells which had been previously coated with KAL protein and incubated in the presence of increasing concentrations of antiserum directed against the KAL protein. The number of adherent cells was calculated as described above. The results of three independent experiments are expressed as the percentage of adherent cells in presence of immune or preimmune sera, relative to the total number of cells deposited in the wells.

Figure 4:
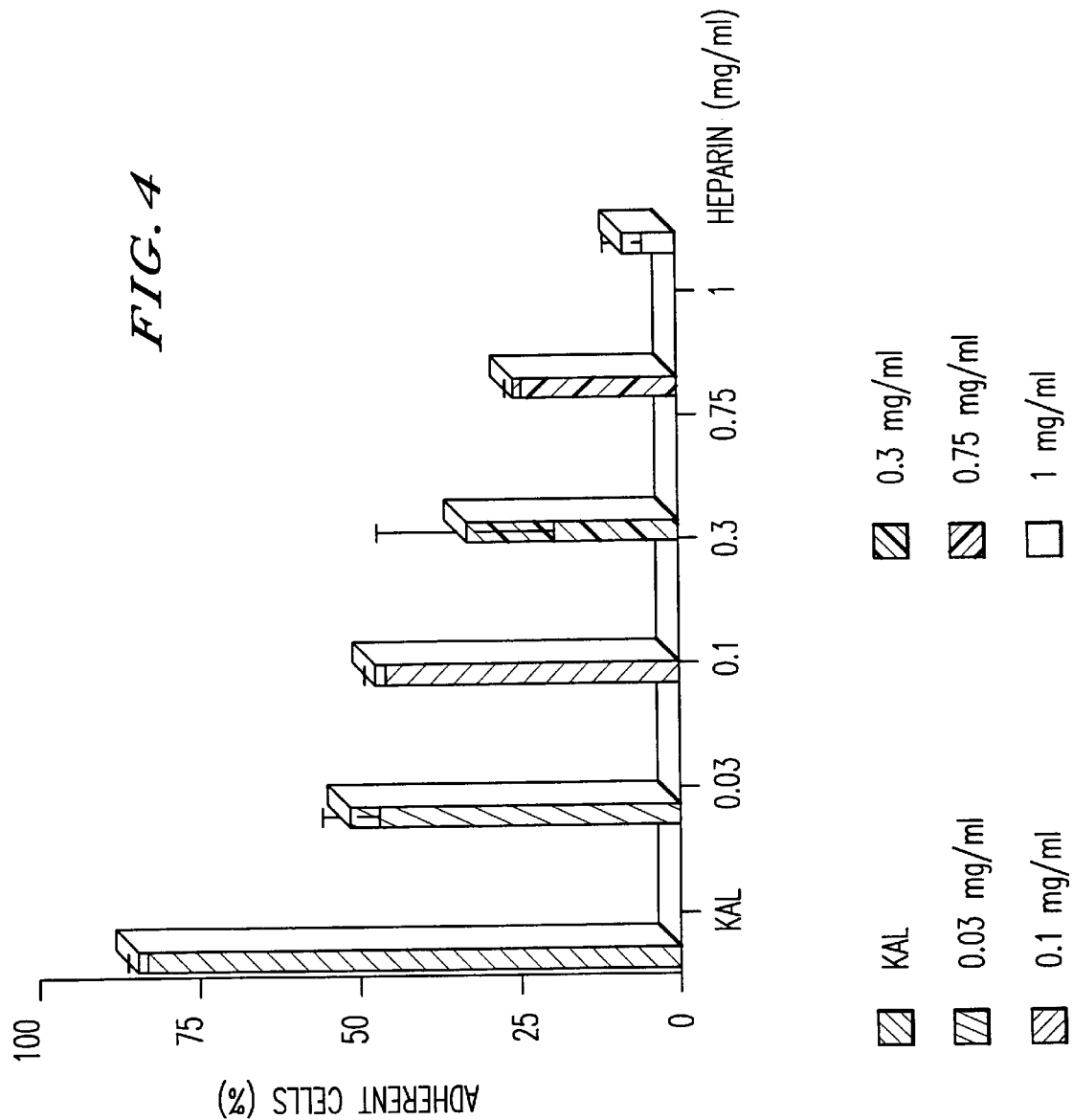

FIG. 4. Adhesion of PC12 cells to the KAL protein was inhibited in the presence of heparin. PC12 cells were added to the wells which had been previously coated with KAL protein and incubated in the presence of increasing concentrations of heparin, and then the number of adherent cells was calculated as described above. The results are expressed as the percentage of adherent cells in absence or in presence of heparin, in relation to the total number of cells deposited on the substratum.

Figure 5:
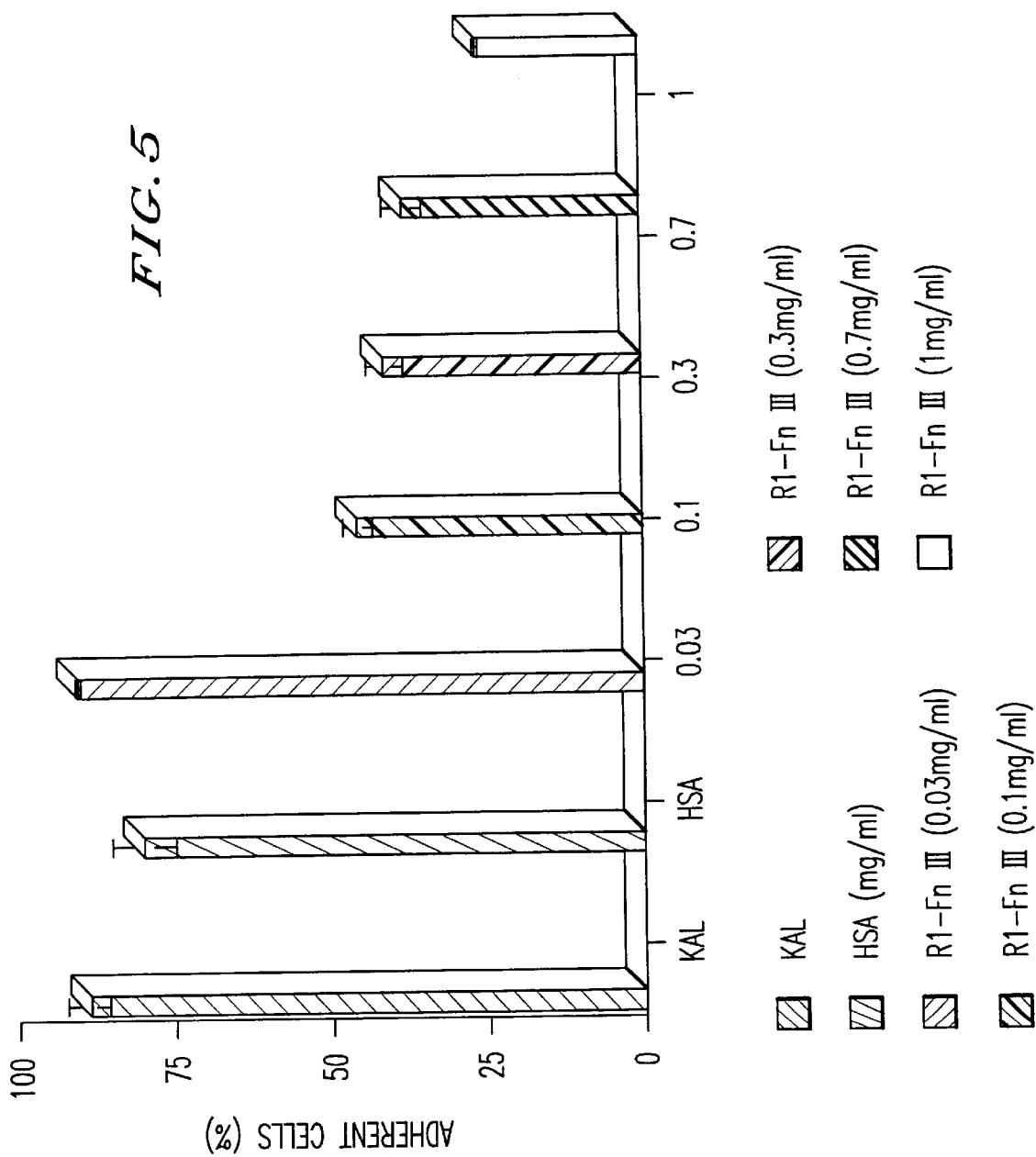

FIG. 5. Adhesion of PC 12 cells to KAL protein was inhibited in the presence of R1-FNIII PC12 cells were incubated with increasing concentrations of R1-FNIII, or human serum albumin (HSA) and added to the wells which have previously been coated with KAL protein. The number of adherent cells was calculated as described above. The results are expressed as the percentage of adherent cells in absence or in presence of R1-FNIII, relative to the total number of cells deposited on the substratum.

FIG. 6: Reaggregates of cerebellar neurons from postnatal day-5 are cultured for 48 h on KAL protein substrate (A), or respectively on positive or negative controls, poly-1-lysine (B), BSA (C). Cells were stained with toluidine blue. Note that KAL protein is a permissive substrate for survival and neurite outgrowth of cerebellar granule cells.

Figure 7A:
Figure 7B:
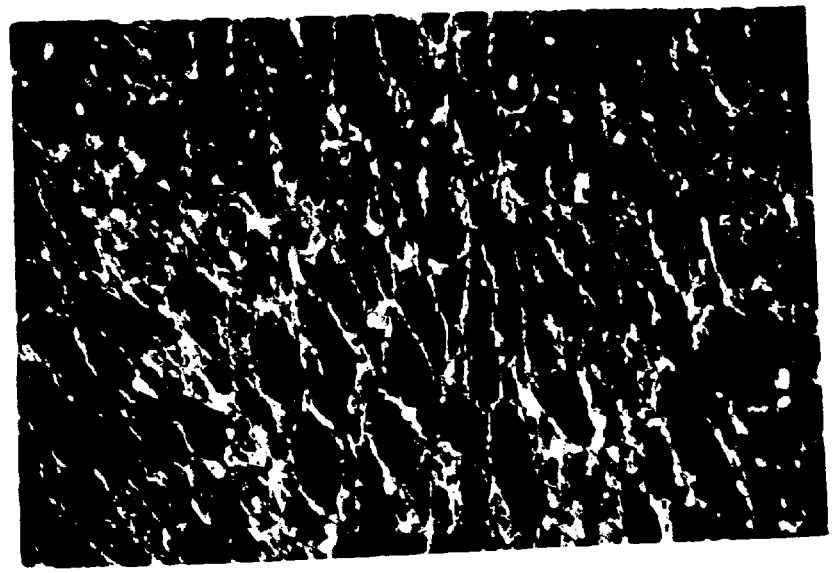
Figure 7C:
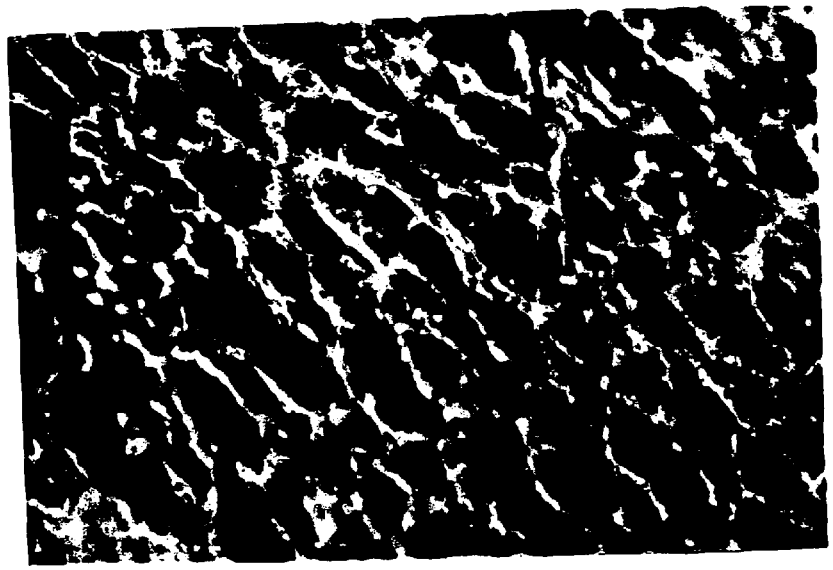

FIG. 7. Immunodetection of the KAL protein expressed in CHO cells. Wild type CHO cells (A), KAL-transfected clone 1—1 (B), and 2–3 (C). Cells were fixed using paraformaldehyde. Note that the immunostaining delineates the cells and displays the expected pattern for an extracellular matrix component.

FIG. 8. Induction of neurite fasciculation from cerebellar cell aggregates by a monolayer of KAL-expressing cells. Aggregates of cerebellar neurons from post-natal day 5 mice were cultured for 24 h on monolayers of either wild type CHO cells (A), or clones of KAL-transfected CHO cells, clone 2–3 (B-D) and clone 1—1 (E and F). Neurites were short and fasciculated on KAL-expressing cells (B, D and F). C and E: in the presence of anti-KAL Fab fragments (0.2 mg/ml) neurite fasciculation was not induced from cell aggregates cultured on KAL-transfected cells. Neurons were stained for GAP 43 immunoreactivity.

Figure 9A:
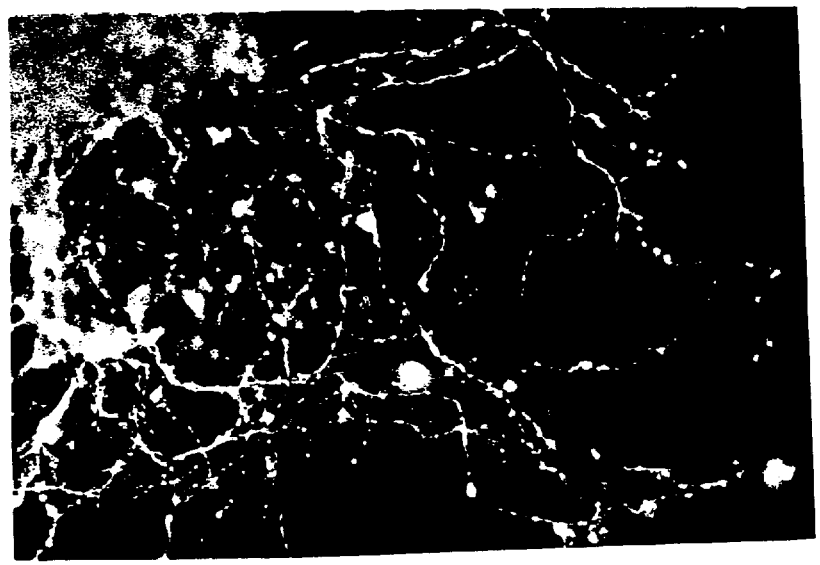
Figure 9B:
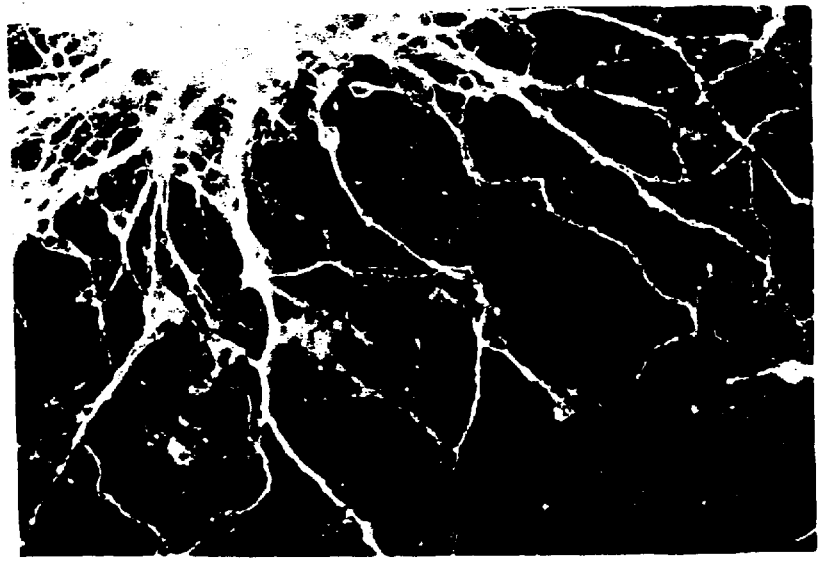
Figure 9C:
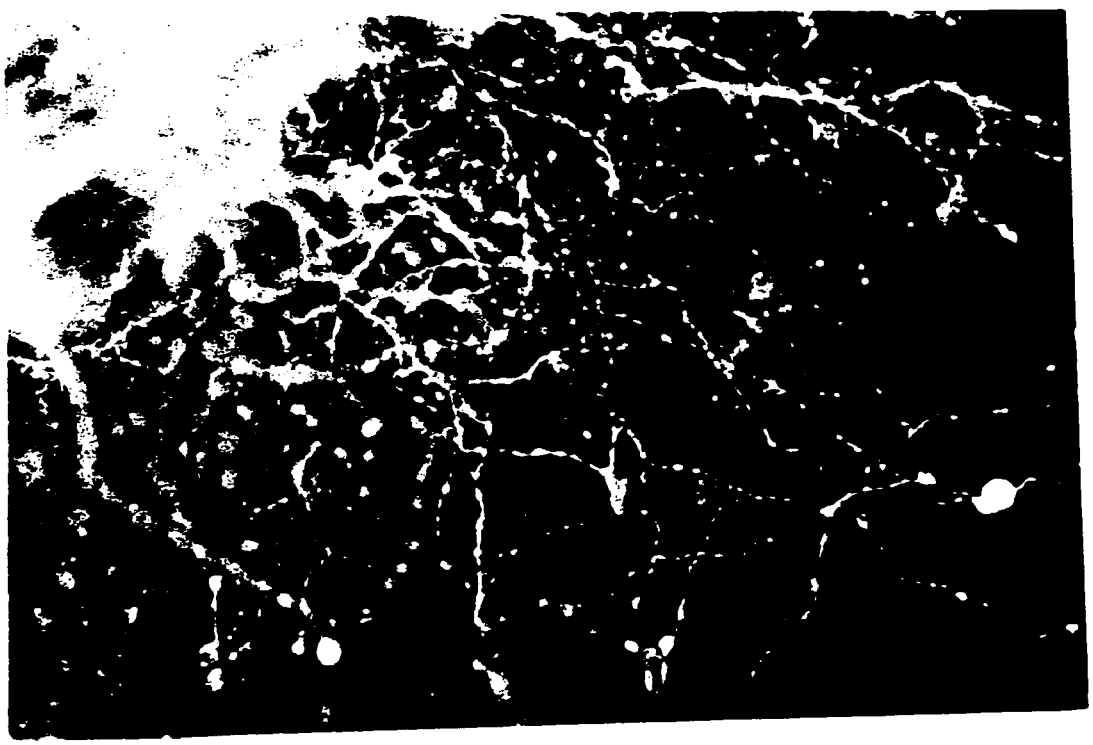

FIG. 9: Aggregates of cerebellar neurons cultured for 24 h on either wild type CHO cells (A) or clones of KAL-transfected CHO cells: clone 2–3 (B and C). Neurite fasciculation observed on KAL-expressing cells (B) is prevented by the addition of anti-KAL Fab to culture medium (C).

Figure 10A:
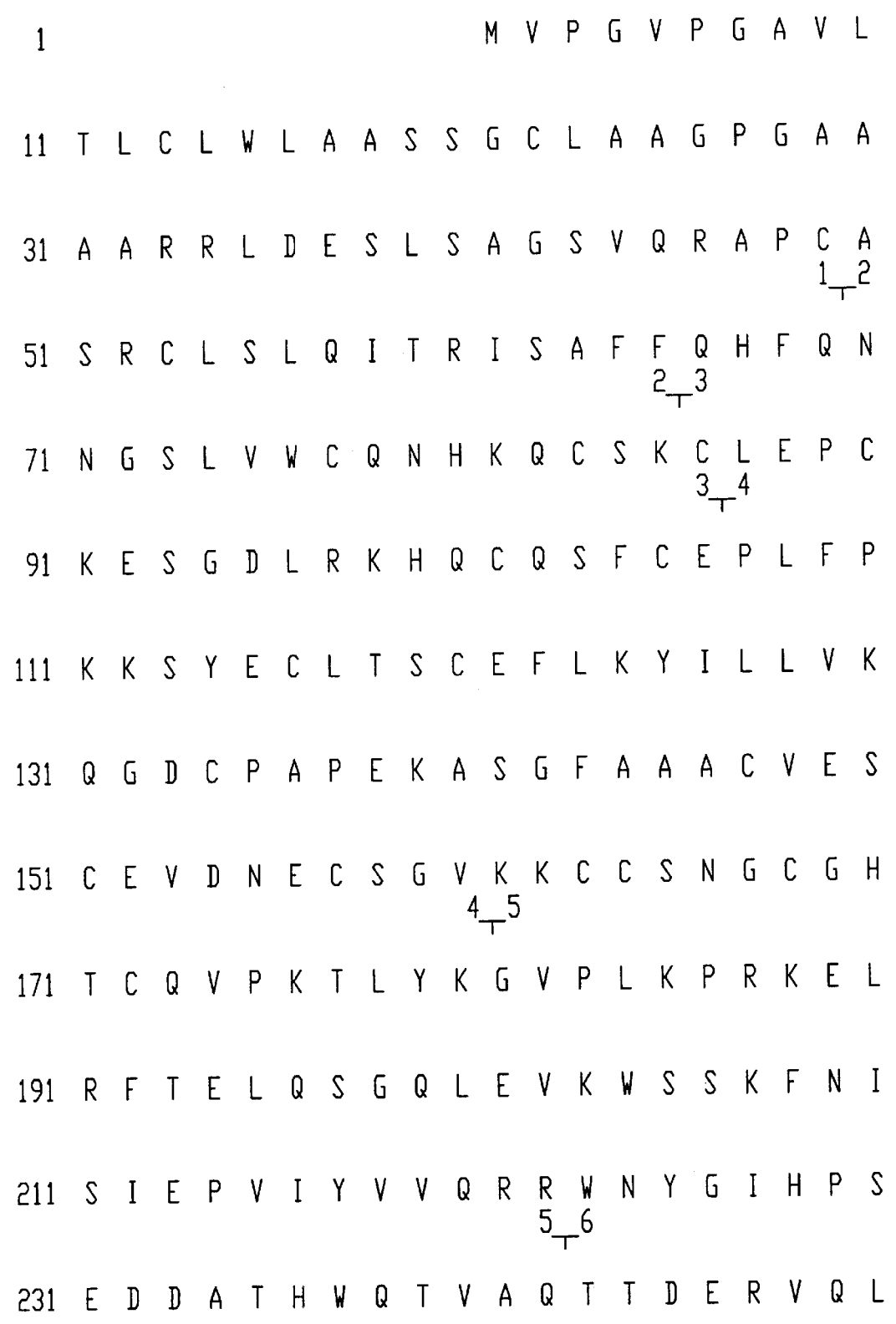
Figure 10B:
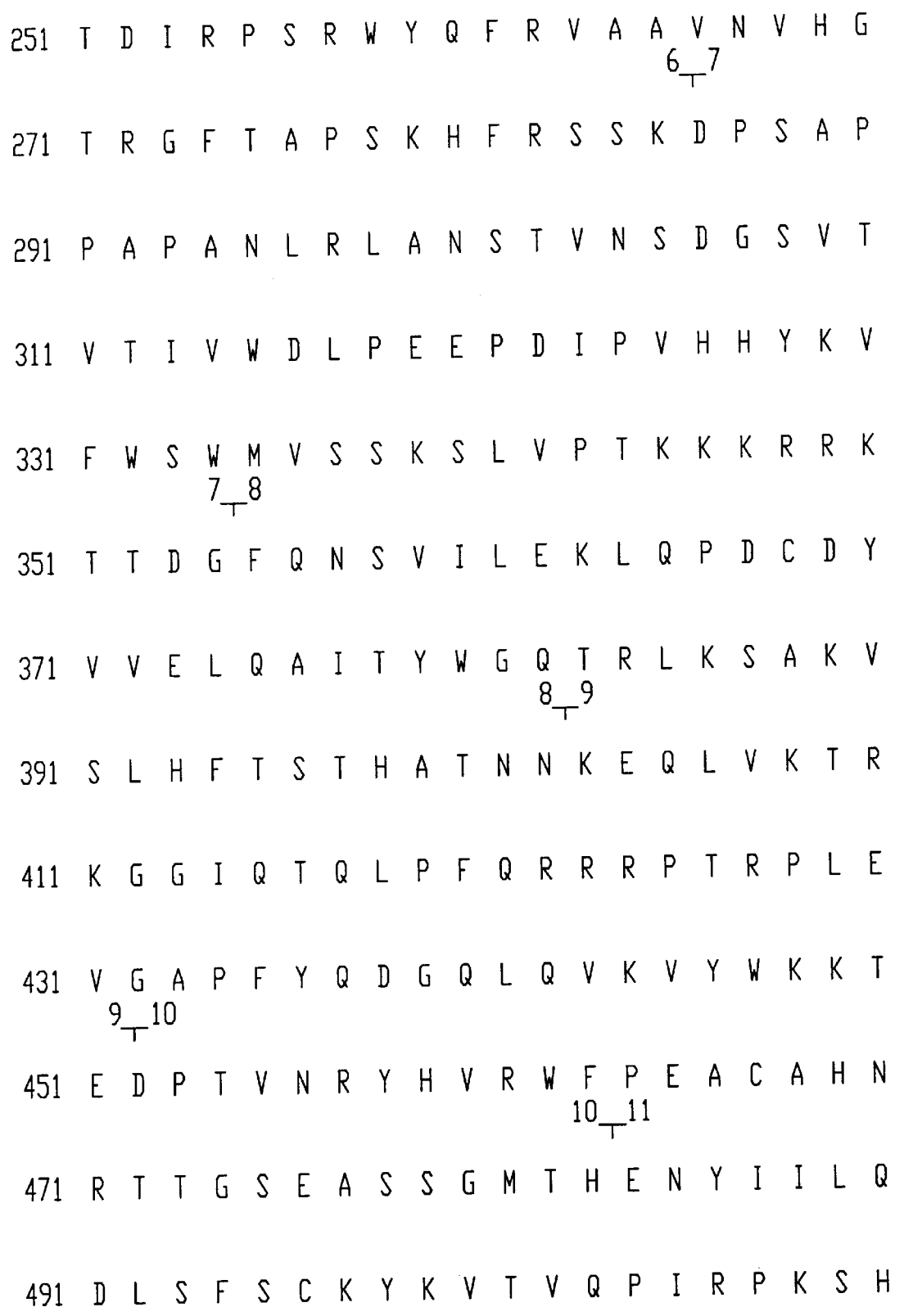
Figure 10C:
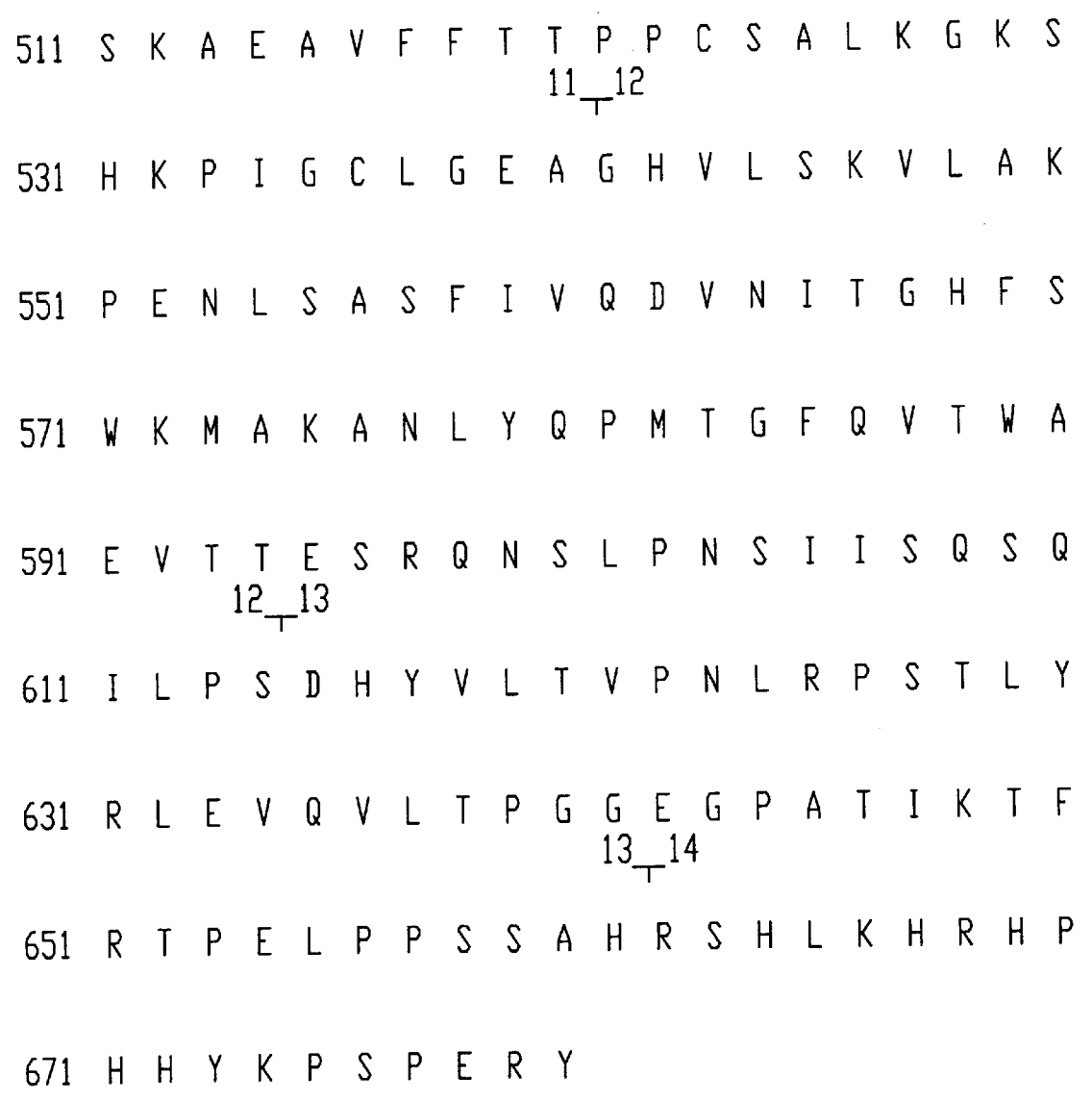
Figure 11:
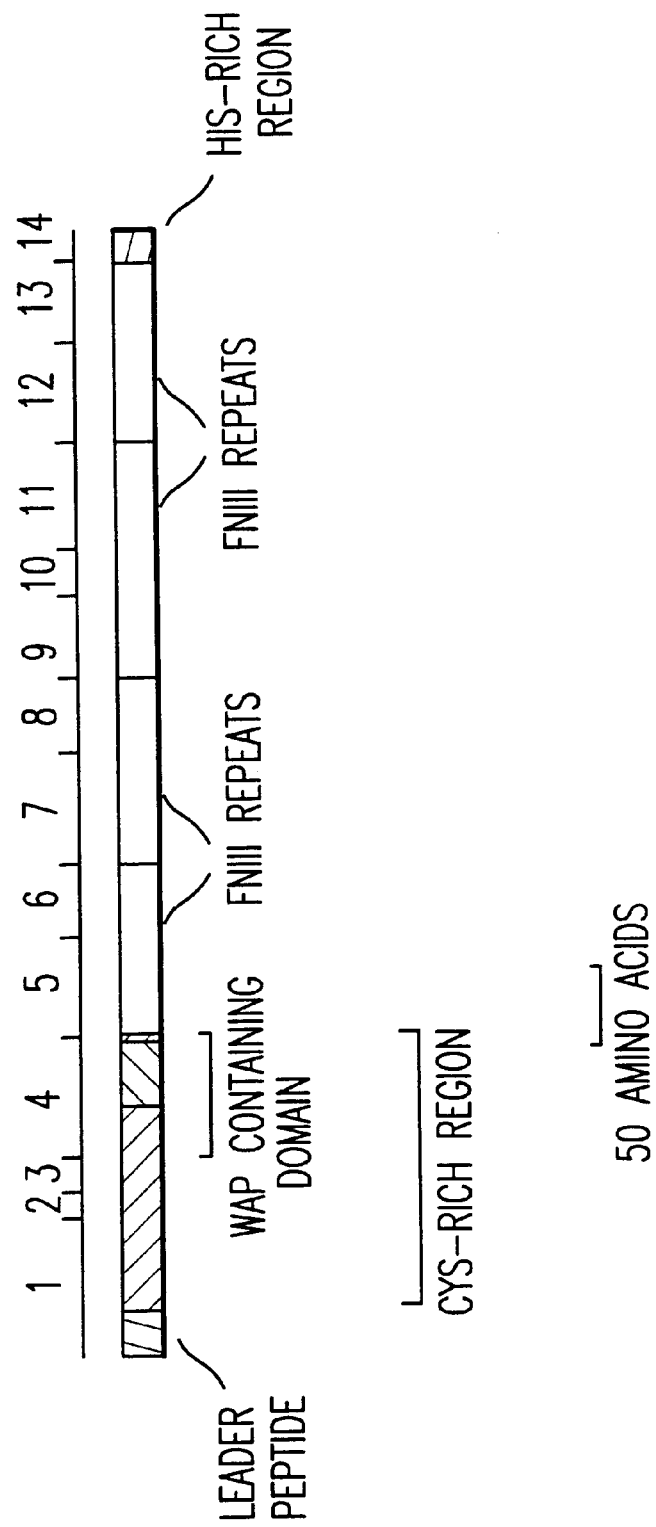

FIGS. 10A thru 10C: Amino acid sequence of the human KAL protein (SEQ ID NO:1), the fibronectin type III repeats are respectively located in the following sequences:

the sequence beginning at aminoacid in position 18? and ending at aminoacid in position 286 of the entire aminoacid sequence of the human KAL protein;

the sequence beginning at aminoacid in position 287 and ending at aminoacid in position 403 of the entire aminoacid sequence of the human KAL protein;

the sequence beginning at aminoacid in position 404 and ending at aminoacid in position 541 of the entire aminoacid sequence of the human KAL protein;

the sequence beginning at aminoacid in position 542 and ending at aminoacid in position 662 of the entire aminoacid sequence of the human KAL protein;

FIG. 11: Schematic representation of the localization of the different domains of the KAL protein.

DETAILED DESCRIPTION OF THE INVENTION

The KAL protein has been produced in transfected eukaryotic cells, and specifically CHO cells. This protein with an approximate molecular mass of 100 kDa is N-glycosylated, secreted in the cell culture medium, and was found to be localized mainly at the cell surface. Therefore, the protein encoded by the KAL gene is likely to be an extracellular matrix component in vivo.

For the purpose of the present invention:

A "gene" refers to the entire DNA portion involved in the synthesis of a protein. A gene embodies the structural or coding portion which begins at the 5' end from the translation start codon (usually ATG) and extends to the stop (TAG, TGA, or TAA) codon at the 3' end. It also contains a promoter region, usually located 5' or upstream to the structural gene, which initiates and regulates the expression of a structural gene. Also included in a gene are the 3' end and poly(A)+addition sequences.

A "structural gene" is that portion of a gene comprising a DNA segment encoding a protein, polypeptide or a portion thereof, and excluding the 5' and 3' non coding sequences. Moreover, since heparin treatment of cell membrane fractions resulted in the release of the protein, we suggest that heparan-sulfate proteoglycans are involved in the binding of the protein to the cell membranes. Polyclonal and monoclonal antibodies directed against the purified protein were generated. They subsequently allowed us to determine the cellular distribution of the protein in the chicken central nervous system at late stages of embryonic development. The protein is present on cell bodies and along neurites of definite neuronal populations including Purkinje cells in the cerebellum, mitral cells in the olfactory bulbs and several neuronal cell populations in the optic tectum and the striatum [Soussi-Yanicostas, 1996].

The N-terminal sequence of the KAL protein is cysteine-rich and can be subdivided into two subregions. The first has no similarity with any known protein. The other fits the consensus whey acidic protein (WAP) 4-disulfide core motif (Dandekar et al., 1982; Hennighausen and Sippel, 1982), a motif shared by several small proteins with serine protease inhibitory activity (Kato and Tominaga, 1979; Seemuller et al., 1986; Stetler et al., 1986; Wiedow et al., 1990). A particular feature of the C-terminus of the protein is the presence of 11 basic (including 6 histidyl) residues among 20 mostly hydrophilic amino acids. The KAL protein contains four contiguous fibronectin type III repeats (del Castillo et al., 1992). This motif has been found in a wide variety of molecules with morphoregulatory roles, most of which are involved in cell adhesion, fasciculation and growth of neurons. Among them, L1/NgCAM (Moos et al., 1988; Burgoon et al., 1991) Nr-CAM/Bravo (Grumet et al., 1991; Kayyem et al., 1992), F3/F11 (Gennarini et al., 1989; Brummendorf and Rathjen, 1993), TAG/Axonin-1 (Furley et al., 1990; Zuellig et al, 1992), Tenascin-R (Norenberg et al, 1995), Tenascin-C (Gotz et al., 1996). Interestingly, the type III repeats of the protein encoded by the KAL gene show even greater similarity with those of cell adhesion molecules such as TAG-1/Axonin-1, L1, and F3/F11 (Brummendorf and Rathjen, 1993) which have been shown to mediate neurite outgrowth or axon-axon interactions [Sonderegger and Rathjen, 1992 #48]. Altogether, the sequence comparisons suggest that the protein encoded by the KAL gene has several functions including protease inhibitory activity and adhesion.

We demonstrate that the purified KAL protein is a cell adhesion molecule that is permissive for neuron growth in vitro and is thus particularly suitable for neuron growth assays in vitro. We also show that transfected CHO cells producing the KAL protein induce axonal fasciculation of cerebellar granule cells cultivated upon this CHO cell monolayer.

These results have allowed the inventors to design specific therapeutic compositions for treating various neuronal or renal disorders using the purified KAL protein or a biologically active derivative of the KAL protein as described above or, as an alternative embodiment, using a polynucleotide encoding for the KAL protein or for one of its biologically active derivative.

In a preferred embodiment of the therapeutic compositions of the present invention, the amount of the biologically active peptide component is comprised in the range from 0.1 µg/ml to 10 µg/ml in the body fluid. The dose-range is expressed in reference to the bioavailability of the KAL protein or of one of its biologically active derivatives at the body site to be treated.

As already mentioned, a particular biologically active part of the KAL protein consists in one or several of the four fibronectin type III repeat of the KAL protein (FIG. 9) alone or in combination one with each other that are obtained by transfection of a procaryotic or an eukaryotic cell, specifically a CHO cell, with the corresponding encoding DNA that has been inserted in a suitable expression vector.

A suitable vector for the expression of the biologically active part of the KAL protein above-defined in baculovirus vector that can be propagated in insect cells and in insect cell lines. A specific suitable host vector system is the pVL 1392/1393 baculovirus transfer vector (Pharmingen) that is used to transfect the SF9 cell line (ATCC No.CRL 1711) which is derived from *Spodoptera frugiperda*.

Another suitable vector for the expression in bacteria and in particular in *E. coli,* is the pQE-30 vector (QIAexpress) that allows the production of a recombinant protein containing a 6xHis affinity tag. The 6xHis tag is placed at the C-terminus of the recombinant KAL protein biologically active part which allows a subsequent efficient purification of the recombinant protein by passage onto a Nickel or Copper affinity chromatography column. The Nickel chromatography column may contain the Ni-NTA resin (Porath et al., 1975).

In another embodiment of the therapeutic composition according to the invention, the said composition comprises a polynucleotide coding for the KAL protein or one of its biologically active derivatives in order to perform a gene therapy.

The gene therapy consists in correcting a defect or an anomaly (mutation, aberrant expression etc.) by the introduction of a genetic information in the affected organism. This genetic information may be introduced in vitro in a cell that has been previously extracted from the organism, the modified cell being subsequently reintroduced in the said organism, directly in vivo into the appropriate tissue.

The method for delivering the corresponding protein or peptide to the interior of a cell of a vertebrate in vivo comprises the step of introducing a preparation comprising a pharmaceutically acceptable injectable carrier and a naked polynucleotide operatively coding for the polypeptide is taken up into the interior of the cell and has a pharmaceutical effect at the renal, retinal or the neuronal level of the vertebrate.

In a specific embodiment, the invention provides a pharmaceutical product, comprising a naked polynucleotide operatively coding for the KAL protein or one of its biologically active derivatives, in solution in a physiologically acceptable injectable carrier and suitable for introduction interstitially into a tissue to cause cells of the tissue to express the said protein or polypeptide.

Advantageously, the therapeutic composition containing a naked polynucleotide is administered locally, near the site to be treated.

The polynucleotide operatively coding for the KAL protein or one of its biologically active derivatives is a vector comprising the genomic DNA or the complementary DNA coding for the KAL protein or its protein derivative and a promoter sequence allowing the expression of the genomic DNA or the complementary DNA in the desired vertebrate cells.

The vector component of a therapeutic composition according to the present invention is advantageously a plasmid, a part of which is of bacterial origin, which carries a bacterial origin of replication and a gene allowing its selection such as an antibiotic resistance gene.

By "vector" according to this specific embodiment of the invention is intended a circular or linear DNA molecule.

This vector may also contain an origin of replication that allows it to replicate in the vertebrate host cell such as an origin of replication from a bovine papillomavirus.

The promoter carried by the said vector is advantageously the cytomegalovirus promoter (CMV). Nevertheless, the promoter may also be any other promoter with the proviso that the said promoter allow an efficient expression of the DNA insert coding for the KAL protein or one of its biologically active derivatives within the host.

Thus, the promoter is selected among the group comprising:

an internal or an endogenous promoter, such as the natural promoter associated with the structural gene coding for KAL; such a promoter may be completed by a regulatory element derived from the vertebrate host, in particular an activator element;

a promoter derived from a cytoskeletal protein gene such as the desmin promoter (Bolmont et al., J. of Submicroscopic cytology and pathology, 1990, 22:117–122; Zhenlin et al., Gene, 1989, 78:243–254).

As a general feature, the promoter may be heterologous to the vertebrate host, but it is advantageously homologous to the vertebrate host.

By a promoter heterologous to the vertebrate host is intended a promoter that is not found naturally in the vertebrate host.

Therapeutic compositions comprising a naked polynucleotide are described in the PCT application No.WO 90/11092 (Viacl Inc.) and also in the PCT application No. WO 95/11307 (Institut Pasteur, INSERM, Université d'Ottawa) as well as in the articles of Tacson et al. (1996, Nature Medicine, 2(8):888–892) and of Huygen et al. (1996, Nature Medicine, 2(8):893–898).

The therapeutic compositions described above may be administered to the vertebrate host by a local route such as an intramuscular route.

The therapeutic naked polynucleotide according to the present invention may be injected to the host after it has been coupled with compounds that promote the penetration of the therapeutic polynucleotide within the cell or its transport to the cell nucleus. The resulting conjugates may be encapsulated in polymer microparticles as it is described in the PCT application No. WO 94/27238 (Medisorb Technologies International).

In another embodiment, the DNA to be introduced is complexed with DEAE-dextran (Pagano et al., 1967, J. Virol., 1:891) or with nuclear proteins (Kaneda et al., 1989, Science 24:375), with lipids (Feigner et al., 1987, Proc. natl. Acad. Sci., 84:7413) or encapsulated within liposomes (Fraley et al., 1980, J. Biol. Chem., 255:10431).

In another embodiment, the therapeutic polynucleotide may be included in a transfection system comprising polypeptides that promote its penetration within the host cells as it is described in the PCT application WO 95/.10534 (Seikagaku Corporation).

The therapeutic polynucleotide and vector according to the present invention may advantageously be administered in the form of a gel that facilitates their transfection into the cells. Such a gel composition may be a complex of poly-L-Lysine and lactose, as described by Midoux (1993, Nucleic Acids Research, 21:871–878) or also poloxamer 407 as described by Pastore (1994, Circulation, 90:I-517). The therapeutic polynucleotide and vector according to the invention may also be suspended in a buffer solution or be associated with liposomes.

Thus, the therapeutic polynucleotide and vector according to the invention are used to make pharmaceutical compositions for delivering the DNA (genomic DNA or cDNA) coding for the KAL protein or one of its biologically active derivatives at the site of the injection.

The amount of the vector to be injected varies according to the site of injection and also to the kind of disorder to be treated. As an indicative dose, between 0.1 and 100 $\mu$g of the vector will be injected in a patient.

In another embodiment of the therapeutic polynucleotide according to the invention, this polynucleotide may be introduced in vitro in a host cell, preferably in a host cell previously harvested from the patient to be treated and more preferably a somatic cell such as a muscle cell, a renal cell or a neurone. in a subsequent step, the cell that has been transformed with the therapeutic nucleotide coding for the KAL protein or one of its biologically active derivative is implanted back into the patient body in order to deliver the recombinant protein within the body either locally or systematically.

In a preferred embodiment, gene targeting techniques are used to introduce the therapeutic polynucleotide into the host cell. One of the preferred targeting techniques according to the present invention consists in a process for specific replacement, in particular by targeting the KAL protein encoding DNA, called insertion DNA, comprising all or part of the DNA structurally encoding for the KAL protein or one of its biologically active derivatives, when it is recombined with a complementing DNA in order to supply a complete recombinant gene in the genome of the host cell of the patient, characterized in that:

the site of insertion is located in a selected gene, called the recipient gene, containing the complementing DNA encoding the KAL protein or one of its biologically active derivatives and in that the polynucleotide coding for the KAL protein or one of its biologically active derivatives may comprise:

"flanking sequences" on either side of the DNA to be inserted, respectively homologous to two genomic sequences which are adjacent to the desired insertion site in the recipient gene.

the insertion DNA being heterologous with respect to the recipient gene, and the flanking sequences being selected from those which constitute the abovementioned complementing DNA and which allow,k as a result of homologous recombination with corresponding sequences in the recipient gene, the reconstitution of a complete recombinant gene in the genome of the eukaryotic cell.

Such a DNA targeting technique is described in the PCT patent application No. WO 90/11354 (Institut Pasteur).

Such a DNA targeting process makes it possible to insert the therapeutic nucleotide according to the invention behind an endogenous promoter which has the desired functions (for example, specificity of expression in the selected target tissue).

According to this embodiment of the invention, the inserted therapeutic polynucleotide may contain, between the flanking sequences and upstream from the open reading frame encoding the KAL protein (or one of its biologically active derivatives), a sequence carrying a promoter sequence either homologous or heterologous with respect to the KAL encoding DNA. The insertion DNA may contain in addition, downstream from the open reading frame and still between the flanking sequences, a gene coding for a selection agent, associated with a promoter making possible its expression in the target cell.

According to this embodiment of the present invention, the vector used also contains a bacterial origin of replication of the type colE1, pBR322, which makes the clonings and preparation in *E.coli* possible. A preferred vector is the plasmid pGN described in the PCT application No. WO 90/11354.

Other gene therapy methods than those using homologous recombination may also be used in order to allow the expression of a polynucleotide encoding the KAL protein or one of its biologically active derivatives within a patient's body.

In all the gene therapy methods that may be used according to the present invention, different types of vectors are utilized.

In one specific embodiment, the vector is derived from an adenovirus. Adenoviruses vectors that are suitable according to the gene therapy methods of the present invention are those described by Feldman and Steg (1996, Medicine/Sciences, synthese, 12:47–55) or Ohno et al. (1994, Sciences, 265:781–784) or also in the french patent application No. FR-94.03.151 (Institut Pasteur, Inserm). Another preferred recombinant adenovirus according to this specific embodiment of the present invention is the human adenovirus type 2 or 5 (Ad 2 or Ad 5) or an adenovirus of animal origin (French patent application No. FR-93.05954).

Among the adenoviruses of animal origin it can be cited the adenoviruses of canine (CA V2, strain Manhattan or A26/6 [ATCC VR-800]), bovine, murine (Mavl, Beard et al., 1980, Virology, 75:81) or simian (SAV).

Preferably, the inventors are using recombinant defective adenoviruses that may be prepared following a technique well-known by one of skill in the art, for example as described by Levrero et al., 1991, Gene, 101:195) or by Graham (1984, EMBO J., 3:2917) or in the European patent application No. EP-185.573. Another defective recombinant adenovirus that may be used according to the present invention, as well as a pharmaceutical composition containing such a defective recombinant adenovirus, is described in the PCT application No. WO 95/14785.

In another specific embodiment, the vector is a recombinant retroviral vector, such as the vector described in the PCT application No. WO 92/15676 or the vector described in the PCT application No. WO 94/24298 (Institut Pasteur). The latter recombinant retroviral vector comprises:

a DNA sequence from a provirus that has been modified such that:

the gag, pol and env genes of the provirus DNA has been deleted at least in part in order to obtain a proviral DNA which is incapable of replicate, this DNA not being able to recombine to form a wild virus;

the LTR sequence comprises a deletion in the U3 sequence, such that the mRNA transcription that the LTR controls is significantly reduced, for example at least 10 times, and the retroviral vector comprises in addition an exogenous nucleotide sequence coding for the KAL protein or one of its biologically active derivatives under the control of an exogenous promoter, for example a constitutive or an inducible promoter.

By exogenous promoter in the recombinant retroviral vector described above is intended a promoter that is exogenous with respect to the retroviral DNA but that may be endogenous or homologous with respect to the KAL protein entire or partial nucleotide coding sequence.

In the case in which the promoter is heterologous with respect to the KAL protein entire or partial nucleotide coding sequence, the promoter is preferably the mouse inducible promoter Mx or a promoter comprising a tetracyclin operator or also a hormone regulated promoter. A preferred constitutive promoter that is used is one of the internal promoters that are active in the resting fibroblasts such the promoter of the phosphoglycerate kinase gene (PGK-1). The PGK-1 promoter is either the mouse promoter or the human promoter such as described by Adra et al. (1987, Gene, 60:65–74). Other constitutive promoters may also be used such that the beta-actin promoter (Kort et al., 1983, Nucleic Acids Research, 11:8287–8301) or the vimentin promoter (Rettlez and Basenga, 1987, Mol. Cell. Biol., 7:1676–1685).

A preferred retroviral vector used according to this specific embodiment of the present invention is derived from the Mo-MuLV retrovirus (WO 94/24298).

In one preferred embodiment, the recombinant retroviral vector carrying the therapeutic nucleotide sequence coding for the KAL protein or one of its biologically active derivatives is used to transform mammalian cells, preferably autologous cells from the mammalian host to be treated, and more preferably autologous fibroblasts from the patient to be treated. The fibroblasts that have been transformed with the retroviral vector according to the invention are reimplanted directly in the patient's body or are seeded in a preformed implant before the introduction of the implant colonized with the transformed fibroblasts within the patient's body. The implant used is advantageously made of a biocompatible carrier allowing the transformed fibroblasts to anchor associated with a compound allowing the gelification of the cells. The biocompatible carrier is either a biological carrier, such as coral or bone powder, or a synthetic carrier, such as synthetic polymer fibres, for example polytetrafluoroethylene fibres.

An implant having the characteristics as defined above is the implant described in the PCT application No. WO 94/24298 (Institut Pasteur).

Another subject of the present invention is a method for screening ligands that bind to the KAL protein.

Such a screening method, in one embodiment, comprises the steps of:
 a) Preparing a complex between the KAL protein and a ligand that binds to the KAL protein by a method selected among the followings:
  preparing a tissue extract containing the KAL protein putatively bound to a natural ligand;
  bringing into contact the purified KAL protein with a solution containing a molecule to be tested as a ligand binding to the KAL protein.
 b) visualizing the complex formed between the KAL protein from the tissue extract and the natural ligand of the KAL protein or the complex formed between the purified KAL protein and the molecule to be tested.

For the purpose of the present invention, a ligand means a molecule, such as a protein, a peptide, a hormone, or antibody or a synthetic compound capable of binding to the KAL protein or one of its biologically active derivatives or to modulate the expression of the polynucleotide coding for the KAL protein or coding for one of its biologically active derivatives.

In the first embodiment of the screening procedure wherein a natural ligand of the KAL protein is to be characterized, it is processed as follows:

A tissue putatively containing the KAL protein bound to its natural ligand, for example the cerebellum, olfactory bulbs, tectum or liver from embryos, especially chicken embryos, are homogenized in 10 mM Hepes, pH 7.4, containing 100 μg/ml PMSF, 200 μg/ml aprotinin and 5 μg/ml Dnase, with a glass-Teflon homogenizer. The homogenate is centrifuged at 1,000 g for 10 minutes; the supernatant is removed and centrifuged at 190,000 g for 30 min at 4° C. The pellet containing the membrane fraction is stored at −20° C. until used.

The cell membrane fractions are incubated first in 0.9% Triton X-100, 0.1% ovalbumin, S mM EDTA, 50 mM Tris-HCl, pH 8, with the P34 immune serum (Soussi-Yanicostas et al., 1996) overnight at 4° C., then with Protein G-sepharose (Pharmacia) for 2 hours. Complexes are centrifuged, washed three times in PBS and three times in 50 mM Tris-Hcl, pH 8. Then the complexes are dissociated in a dissociating buffer containing SDS in order to dissociate the KAL protein from its bound natural ligand. Immunoprecipitates are analysed by western blot following the technique described by Gershoni and Palade (1983, Anal. Biochem., 131:1–15). The anti-KAL protein monoclonal antibody produced by the hybridome clone 1–4 was used to detect the KAL protein and a panel of candidate antibodies, for example antibodies directed against different sub-units of integrins are used (at a concentration of 1.5 μg/ml) to identify the ligand that was previously bound to the KAL protein in the tissue extract. IgG peroxidase-conjugated antibody (Bio-Rad, ⅙,000 dilution) is used as second antibody. The blots are revealed by chemiluminescence with the ECL kit (Amersham France).

In a second embodiment of the ligand screening method according to the present invention, a biological sample or a defined molecule to be tested as a putative ligand of the KAL protein is brought into contact with the purified KAL protein, for example the purified recombinant KAL produced by the clone CH KAL 2–3/dl, in order to form a complex between the KAL protein and the putative ligand molecule to be tested. The biological sample may be obtained from a cerebellum or a renal extract, for example.

When the ligand source is a biological sample, the complexes are processed as described above in order to identify and characterize the unknown ligand.

When the putative ligand is a defined known molecule to be tested, the complexes formed between the KAL protein and the molecule to be tested are not dissociated prior to the western blotting in order to allow the detection of the complexes using polyclonal or monoclonal antibodies directed against the KAL protein.

In a particular embodiment of the screening method, the putative ligand is the expression product of a DNA insert contained in a phage vector (Parmley and Smith, Gene, 1988, 73:305–318). According to this particular embodiment, the recombinant phages expressing a protein that binds to the immobilized KAL protein is retained and the complex formed between the KAL protein and the recombinant phage is subsequently immunoprecipitated by a polyclonal or a monoclonal antibody directed against the KAL protein.

According to this particular embodiment, a ligand library is constructed in recombinated phages from human of chicken genomic DNA or cDNA. Once the ligand library in recombinant phages has been constructed, the phase population is brought into contact with the immobilized KAL protein. The preparation of complexes is washed in order to remove the non-specifically bound recombinant phages. The phages that bind specifically to the KAL protein are then eluted by a buffer (acid pH) or immunoprecipitated by the monoclonal antibody produced by the hybridoma anti-KAL, clone 1,4, and this phage population is subsequently amplified by an over-infection of bacteria (for example E. coli). The selection step may be repeated several times, preferably 2–4 times, in order to select the more specific recombinant phage clones. The last step consists in characterizing the protein produced by the selected recombinant phage clones either by expression in infected bacteria and isolation, expressing the phage insert in another host-vector system, or sequencing the insert contained in the selected recombinant phages.

One group of the numerous candidate ligands that may be screened belong to the integrin protein family.

Another subject of the present invention is a method for screening molecules that modulate the expression of the KAL protein. Such a screening method comprises the steps of:
 a) cultivating a prokaryotic or an eukaryotic cell that has been transfected with a nucleotide sequence encoding the KAL protein, placed under the control of its own promoter;

b) bringing into contact the cultivated cell with a molecule to be tested;

c) quantifying the expression of the KAL protein.

Using DNA recombinant techniques well known by the one skilled in the art, the KAL protein encoding DNA sequence is inserted into an expression vector, downstream from its promoter sequence, the said promoter sequence being described by Cohen-Salmon et al. (1995, Gene, 164:235–242).

The quantification of the expression of the KAL protein may be realized either at the mRNA level or at the protein level. In the latter case, polyclonal or monoclonal antibodies may be used to quantify the amounts of the KAL protein that have been produced, for example in an ELISA or a RLA assay.

In a preferred embodiment, the quantification of the KAL mRNA is realized by a quantitative PCR amplification of the cDNA obtained by a reverse transcription of the total mRNA of the cultivated KAL-transfected host cell, using a pair of primers specific for KAL of the kind that are described in the PCT application No. WO 93/02267 (Institut Pasteur, HHS).

As an illustrative example, a pair of primers used to quantitate KAL reverse-transcribed mRNA is the following:
Primer 1 (SEQ ID NO:2): 5'CAG CCA ATG GTG CGG CCT CCT GTC C 3'
Primer 2 (SEQ ID NO:3): 5'TCC CGG CAG ACA GCG ACT CCGT 3'.

The process for determining the quantity of the cDNA corresponding to the KAL mRNA present in the cultivated KAL-transfected cells is characterized in that:

1) a standard DNA fragment, which differs from the KAL cDNA fragment, obtained by the reverse transcription of the KAL-mRNA, but can be amplified with the same oligonucleotide primers is added to the sample to be analyzed containing the KAL-cDNA fragment, the standard DNA fragment and the KAL-cDNA fragment differing in sequence and/or size by not more than approximately 10%, and preferably by not more than 5 nucleotides by strand, 2) the KAL-cDNA fragment and the standard DNA fragment are coamplified with the same oligonucleotide primers, preferably to saturation of the amplification of the KAL-cDNA fragment, 3) to the reaction medium obtained in step 2), there are added:

either two types of labeled oligonucleotide probes which are each specific for the KAL-cDNA fragment and the standard DNA fragment and different from said oligonucleotide primers of step 2), and one of more additional amplification cycle(s) with said labeled oligonucleotide primer(s) is/are performed, so that, during a cycle, after denaturation of the DNA, said labeled oligonucleotide primer(s) hybridize(s) with said fragments at a suitable site in order than a elongation with the DNA polymerase generates labeled DNA fragments of different sizes and/or sequences and/or with different labels according to whether they originate from the DNA fragment of interest or the standard fragment, respectively, and then 4) the initial quantity of KAL-cDNA fragment is determined as being the product of the initial quantity of standard DNA fragment and the ratio of the quantity of amplified KAL-cDNA fragment, which ratio is identical to that of the quantities of the labeled DNA fragments originating from the amplified KAL-cDNA fragment, respectively, obtained in step 3.)

Primers and probes hybridizing with teh KAL-cDNA fragment and used in the above-described quantitative PCR amplifications reaction are described in the PCT application No. WO 93/07267 9institut pasteur, HHS).

More techanical details regarding the performing of the quantitative PCR amplification reaction are found in the PCT application No. WO 93/10257 (Institut Pasteur, Inserm).

Materials and Methods

Antibodies

Immunoglobulins from pre-immune and anti-human Kal rabbit sera were purified by affinity chromatography on protein-A sepharose (Pharmacia Biotech., Sweden). Fragments with an antigen-binding site (Fab) were prepared by proteolytic digestion with papain-agarose (Sigman, USA), undigested IgG were eliminated by protein-A sepharose chromatography and Fab were extensively dialyzed against PBS.

Cell Culture

All the culture media, fetal calf serum (FCS) and horse serum were purchased from Life Technologies (France).

Recombinant CHO cell lines. The 2,4 kb EcoRI insert from the Blue script plasmid p85 (Legouis et al., 1991, Cell, 67:423–435) consisting of the entire 2,040 bp coding region of the human KAL cDNA (GenBank accession number M97252), as well as 56 bp and 293 bp of the 5' and 3' non coding regions, respectively, was introduced, downstream of the CMV/T7 promoter, into a modified pFR400 vector (Genentech Inc., San Francisco, Calif.), pFRCM, that contains a mouse mutant dihydrofolate reductase (dhfr) cDNA. The above-defined p85B plasmid contains a cDNA having the sequence of FIG. 9 and has been deposited at the CNCM (Collection Nationale de Cultures de microorganismes) on Sep. 26, 1991 under the accession number No. I-1146. This pFRCM-KAL construct was transfected into dhfr+CHO cells by calcium phosphate precipitation (Wigler et al., 1979, Cell, 16:777–785). CHO cells were cultivated in Dulbecco's modified Eagle's medium (DMEM) supplemented with 8% fetal calf serum 9Jacques Boy, France). Several independent clones producing KALc were obtained by stepwise selection in increasing concentrations of methotrexate (from 0.3 $\mu$M to 1 mM) as previously described 9Kaufman and Sharp, 1982, J. Mol. Biol., 159:301–621). Expression of KALc was assessed at each step by immunocytolabeling using a polyclonal antibody that has been prepared against the human KAL protein. Clone CHKAL2–3/dll, which is a subclone of the clone CHO-CAL 2.3 was specifically selected. The parental CHO cell line and the human Kal-transfected CHO clones (1—1 and 2–3) were maintained in DMEM supplemented with 8% FCS, 50 UI/ml penicillin and 50 $\mu$g/ml streptomycin.

Cerebellar cell cultures. Dissociated cell cultures were obtained from Swiss mouse cerebella on postnatal day 5. At this age, granule cells account for up to 90% of the total cell population, glial cells included. Cells were dissociated by combined trituration and trypsinisation, and grown in chemically defined medium DMEM/Ham's F12 (3 vol/1 vol) containing 0.2 mM glutamine, 5 $\mu$g/ml insulin, 100 $\mu$g/ml tranferrin, 20 nM progesterone, 100 mM purrescine, 30 nM selenium 100 U/ml penicillin and 0.1 mg/ml streptomycin.

Reaggregate cultures of cerebellar neurons from mice on postnatal day-5 were prepared according to Gao et al. (1995). After dissocation, cells were further purified by preplating on a poly-L-Lysine treated (25 $\mu$g/ml) substrate for 30 min and plated in uncoated 96-well dishes (5 $10^5$ cells/well) in BME plus 10% horse serum, 5% fetal calf serum, 9 mg/ml glucose, 0.3 mg/ml glutamine, 50 U/ml penicillin and 0.1 mg/ml streptomycin. Aggregates (100–200 cells) were harvested after 24 h to be used in coculture experiments.

Parental and transfected CHO cells (clones 1.1 and 2.3) were seeded in Nunc 8-well labtek slides at a density of $10^4$ cells/well. Cells were grown for 24 h until confluency and used as monolayer underlying aggregated cerebellar neurons. Cocultures were established by adding approximately 50 aggregates/labtek well, and maintained for 24 h or 48 h in defined medium prior to fixation and immunostaining. Where indicated, pre-immune or anti-KAL Fab fragments at a concentration of 0.2 mg/ml were included for the entire coculture period.

Indirect immunofluorescence. For the visualization of neurons grown on monolayers, cells were fixed with 4% paraformaldehyde in phosphate buffer saltine (PBS) for 15 min permeabilized with methanol/acetone for 2 min, rehydrated in PBS, incubated with anti-GAP 43 antiserum (Williams et al., 1992, J. Cell Biol. 119 p.885–892) diluted (1:500) in PBS containing 3% bovine serum albumin (BSA) for 1 h, rinsed with PBS, incubated with Texas-red conjugated anti-rabbit immunoglobulin (specific for Fc fragment) diluted (1:100) in PSB containing 3% BSA for 1 h. After washing with PBS, cells were mounted in Mowiol (Calbiochem, USA). Recombinant KAL protein expressed by clones 1.1 and 2.3 was labeled with anti-KAL IgG (dilution 10 μg/ml) after cell fixation with 4% paraformaldehyde in PBS for 15 min and using the same immunofluorescent staining procedure.

Production and purification of KAL protein The KAL protein was purified from CHKAL2–3/dll cells by a three step procedure including two chromatographies. The cells were washed in $Ca^{2+}$- and $Mg^2$ -free PBS and incubated for 30 min in DMEM supplemented with 350 mM NaCl. The cell supernatant was supplemented with 0.5% of 3-((3-cholamidopropyl)-dimethylammonio)-1-propane-sulfonate (CHAPS), 50 μg/ml phenylmethylfulfonyl fluoride (PMSF), 100 μg/ml pepstatin and 100 μg/ml leupeptin, and then loaded onto a heparin-Sepharose column (HiTRAP™ Heparin, Pharmacia). NaCl elution fractions were loaded onto an immobilized copper adsorption chromatography column (HiTRAP™ chelating $CU^{2+}$, Pharmacia) and the protein was eluted as a single peak at 75 mM imidazole.

Adhesion Assay 24-well microtiter plates were coated at 37° C. overnight with 20 μg/ml of laminin, 5 μg/ml of KAL in PBS, pH=7.4. The plates were washed twice with PBS and non specific sites were blocked by the addition of 1% BSA in PBS for 1 hour at 37° C. Wells were washed twice with PBS. Cerebellar neurons or PC12 cells were resuspended in DMEM to a final concentration of $10^6$ cells/ml. 500 μl of this suspension was added to each coated well. Cells were also added to control wells that had been coated with BSA alone. Plates were incubated at 37° C. for 90 min in a 5% CO2 humidified atmosphere. The wells were washed gently twice with 0.5 ml PBS. To remove adherent cells from the wells, 0.5 ml of 0.05% trypsin-EDTA were added to each well. After 10 min at 37° C., the 0.5 ml of trypsin-EDTA containing the detached cells were removed and the number of cells was determined by using a cell counter (Coutler, ZM equipped with a Coultronic 256 channelizer).

Each cell adhesion assay was carried out in triplicate. The ration of adherent cells with respect to the total number of cell ×100 was determined as the % of cell adhesion.

Antibodies Inhibition Assays

For inhibition of cell adhesion, $5 \times 10^5$ PC12 cells were deposited on areas previously coated with KAL and with antiserum directed against the human KAL protein at different concentrations and treated as described for adhesion assay. Each inhibition assay was performed three times in three independent experiments.

Heparin inhibition assays

PC12 cells (Greene et al., 1076, Proc. Natl. Acad. Sci. USA, 73: 2424–2428) were added to the wells coated with the KAL protein in the presence of different concentrations of heparin and treated as described for adhesion assays. The assays were performed in triplicate.

Competitive inhibition of KAL-mediated adhesion with fusion protein

Human serum albumin fusion protein covering the first repeat of fibronectin type III of KAL protein (R1-FNIII) was produced in yeast. The PC12 cells were incubated with different concentrations of R1-FN111, or with Human Serum Albumin (HSA), or with PBS, for 30 min at 37° C. and added to wells which were coated with KAL protein (5 μg/ml) as described above. The assays were performed in triplicate.

Results

It has been hypothesized that the KAL protein mediates cell adhesion because of its structural similarity with well characterized cell adhesion molecules described by Edelman and Crossin, in 1991. In order to test this hypothesis, we examined the ability of the KAL protein coated on a plastic surface to promote adhesion of cerebellar granule neurons and PC12 cells.

Figure 1:
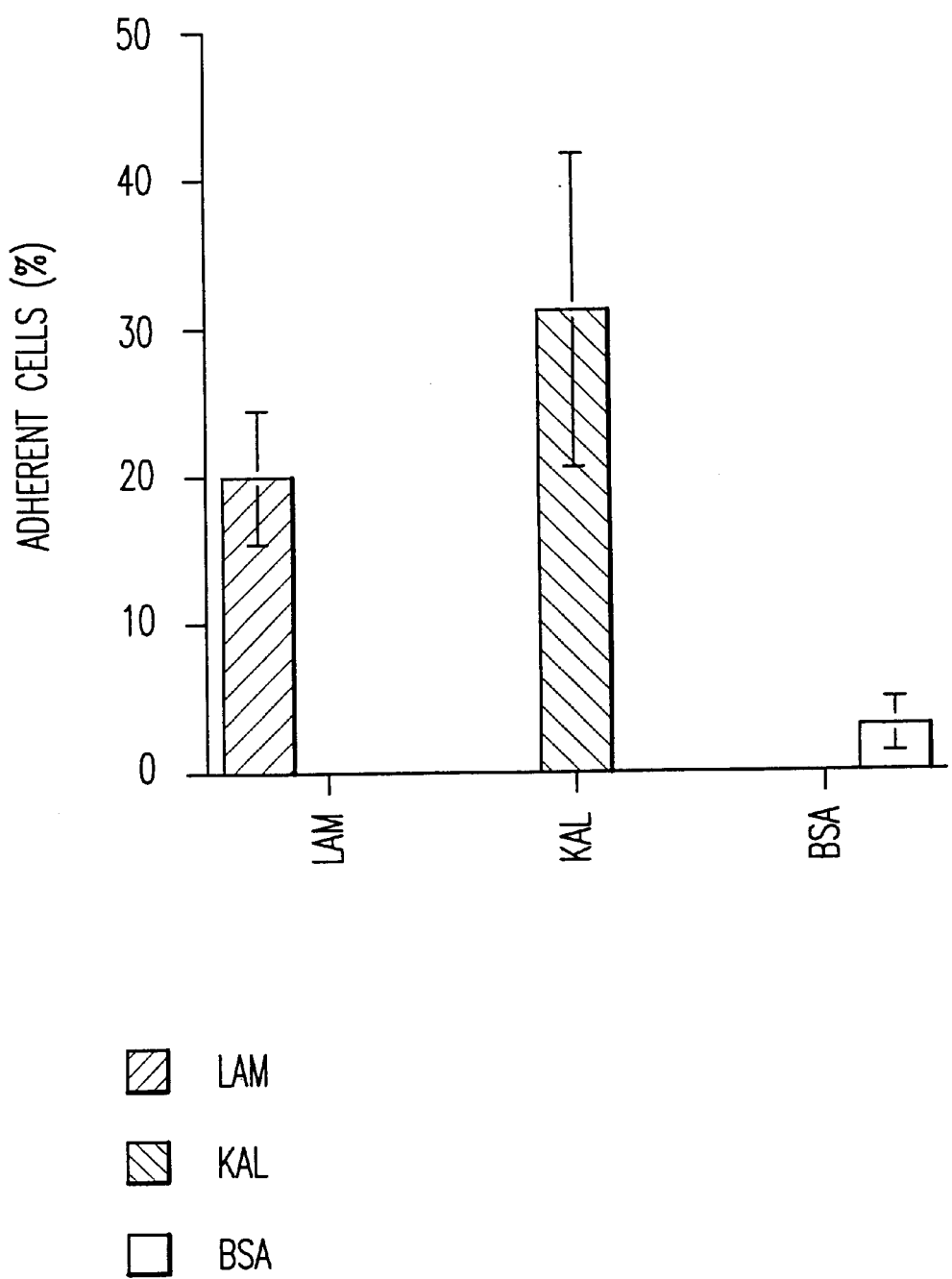
FIG. 1. The KAL protein promotes the adhesion of cerebellar granule cells. Cerebellar granule cells were isolated from postnatal day-5 mice were plated on plastic surfaces which were coated with KAL protein, or with BSA, or with laminin for 90 min at 37° C. as described in Materials and Methods. The wells were washed three times with PBS and the adherent cells were counted as described in Materials and Methods. Similar results were obtained in three separate experiments.

KAL protein isolated from transfected CHO cells was purified by two successive chromatographies on heparin-Sepharose and immobilized copper adsorption columns [Soussi-Yanicostas, 1996 #45] and the purified protein was coated onto Petri dishes. Laminin and bovine serum albumin (BSA) were used as positive and negative controls, respectively. Dissociated mouse cerebellar cells were plated on dishes coated with either KAL protein or laminin, or BSA. After a 90 minute incubation, 80% of the cerebellar neurons were found to adhere to the KAL coated surface. A similar percentage of cell adhesion was observed with laminin-coated dishes. In contrast, no adhesion was detected on BSA Substrate (FIG. 1). Similar results were observed using PC12 cells (FIG. 2). A maximum percentage of cell adhesion was obtained with a concentration of 5 μg/ml of KAL protein (results not shown).

These data suggest that both cerebellar neurons and PC12 cells have the ability to adhere to KAL substrate.

In order to verify that the KAL protein plays a specific role in this cell adhesion, an adhesion assay was performed in the presence of an antiserum directed against the human KAL protein in the culture medium. As shown in FIG. 3, the addition of anti-KAL antibodies inhibits the adhesion of the PC12 cells to KAL-coated dishes. In contrast, the addition of pre-immune serum to the adhesion assay, had no effect on the adhesion of PC12 cells to the KAL protein (FIG. 3).

To test whether the interactions of neural cells with KAL protein can be inhibited by addition of soluble glycosaminoglycans, we tested the ability of PC12 cells to adhere to KAL substrates in the presence of heparin. We observed that adhesion of PC12 cells to KAL protein was inhibited from 0.03 mg/ml of heparin (FIG. 4). These results suggest that heparan-sulfateproteoglycans may be involved in the PC12 cell adhesion to KAL protein.

To investigate the involvement of different domains of KAL protein in PC12 cell adhesion, we produced a human serum albumin fusion protein containing the first repeat of fibronectin type III of the KAL protein (R1-FNIII) in yeast, corresponding, from N-terminal end to C-terminal end, to the aminoacid sequence beginning at the aminoacid at position 182 from the sequence of FIG. 9 and ending at the aminoacid at position 286 from the sequence of FIG. 9. Increasing concentrations of R1-FNIII were incubated with PC12 cells for 30 min at 37° C. before adhesion assays on KAL protein. We observed that R1-FNIII perturbs partially the adhesion of PC12 cells to KAL protein (FIG. 5).

In summary, the cell adhesion assays demonstrated that the KAL protein contains binding sites for molecules present at the cell surface of both cerebellar neurons and PC12 cells. The adhesion of neural cells to KAL protein may depend on glycosaminoglycans. The fiirst fibronectin type III domain of the KAL protein partially account for the binding activity of the molecule.

The purified KAL protein is a permissive substrate for neurite outgrowth of cerebellar neurons.

Figure 6A:
Figure 6B:
Figure 6C:

In order to determine the role of purified KAL protein on neurite outgrowth, we used granule cell aggregates as a model, prepared as described in the Materials and Methods section. Cerebellar granule neurons were seeded on surfaces that had been coated with KAL protein. Polylysine and bovine serum albumin (BSA) were used as positive and negative controls respectively. When aggregates were cultured for 48 hours on KAL protein, neurons remained tightly aggregated and displayed a large halo of neuritic processes (FIG. 6A). A similar observation was obtained on the polylysine-coated surface (FIG. 6B). In contrast, no neuronal survival was observed on the BSA-coated surface (FIG. 6C).

These results show that the KAL protein is a permissive substrate for survival and neurite outgrowth of cerebellar granule neurons.

KAL immunofluorescencestaining at the surface of transfected CHO cells

The different human KAL-expressing CHO cell lines were labeled by indirect immunofluorescence using an antiserum directed against the human KAL gene product. Large amounts of the KAL protein were observed at the cell surface of clonal KAL transfected cell lines 1—1 and 2-3 (FIG. 7).

Figure 8A:
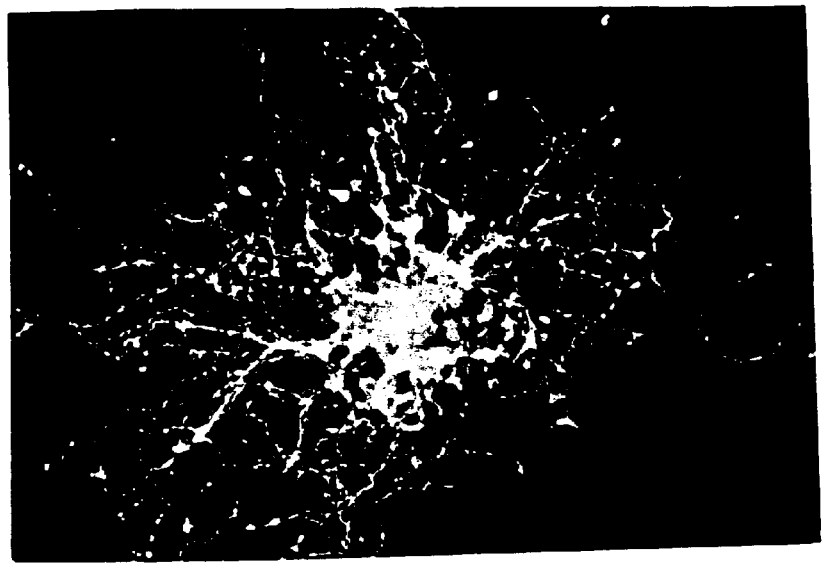
Figure 8B:
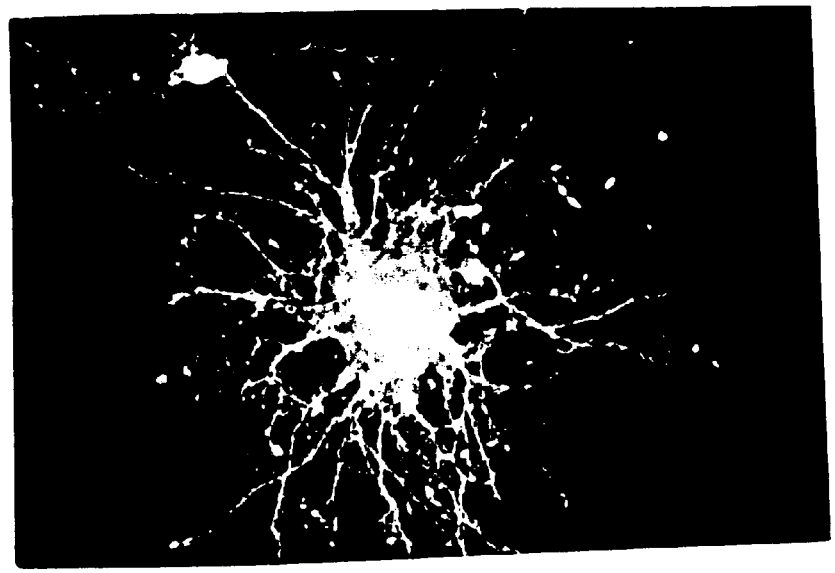

Induction of neurite fasciculation from granule cell aggregates by KAL-expressing cells Granule cell aggregates from post-natal day-5 mice were grown in defined medium onto monolayers of CHO cells. After 24 h of coculture, aggregates had produced long, sinuous, and unfasciculated processes onto control cells (FIGS. 8A and 9A). By contrast, aggregates grown onto KAL-expressing cells displayed short, radial and highly fasciculated neurites (FIGS. 8B and 9B). To ensure that this effect was not an artifact of one particular KAL-expressing cell line, two independent clones (1—1 and 2-3) were tested. They were producing equivalent amounts of the transfected protein as assayed by Western blot. These two clones exhibited the same ability to both fasciculate and reduce length of the neuritic processes growing from granule cell aggregates (FIGS. 8D and F).

Antibody reversal of KAL-induced neurite fasciculation from granule cell aggregates In order to demonstrate the specificity of Kal's effect on fasciculation and growth inhibition of neurites, anti-KAL fragments (0.2 mg/ml) were included during the entire time of coculture of KAL-expressing cells and granule cell aggregates. KAL-expressing monolayers displayed intense staining with anti-KAL Fab as revealed with Texas-red conjugated IgG specific anti-rabbit antibody (same as FIGS. 7B and C, not shown). Both antibodies directed against human KAL and the neuronal marker GAP-43 have been raised in rabbit. Thus, to avoid monolayer staining, neurons were visualized using anti-GAP-43 and Fc-specific Texas red conjugated anti-rabbit antibody.

Figure 8C:
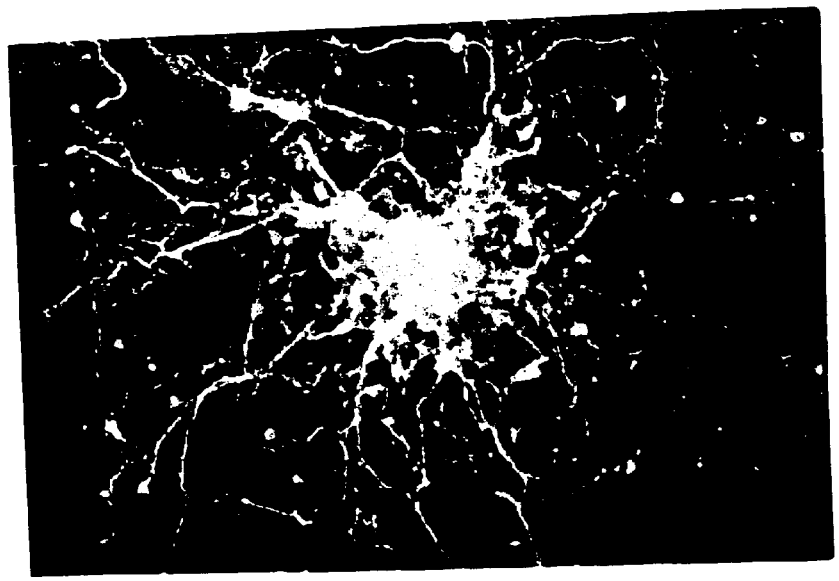
Figure 8D:
Figure 8E:
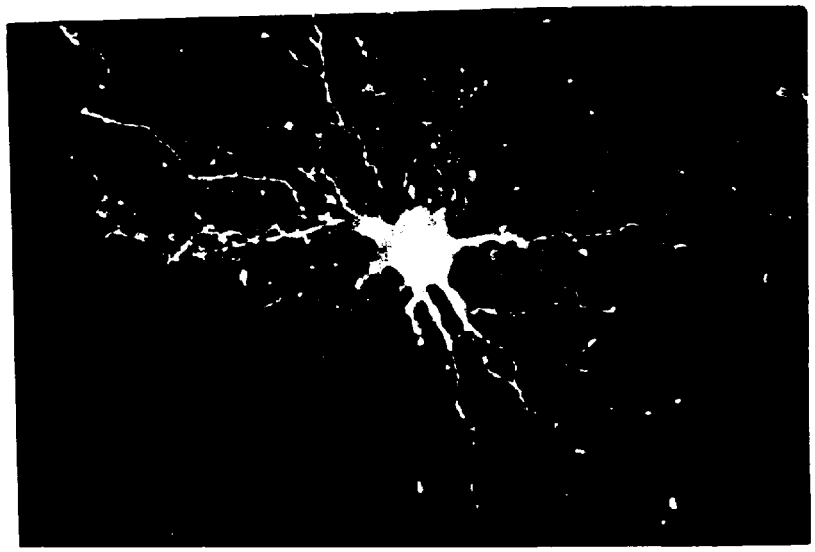
Figure 8F:
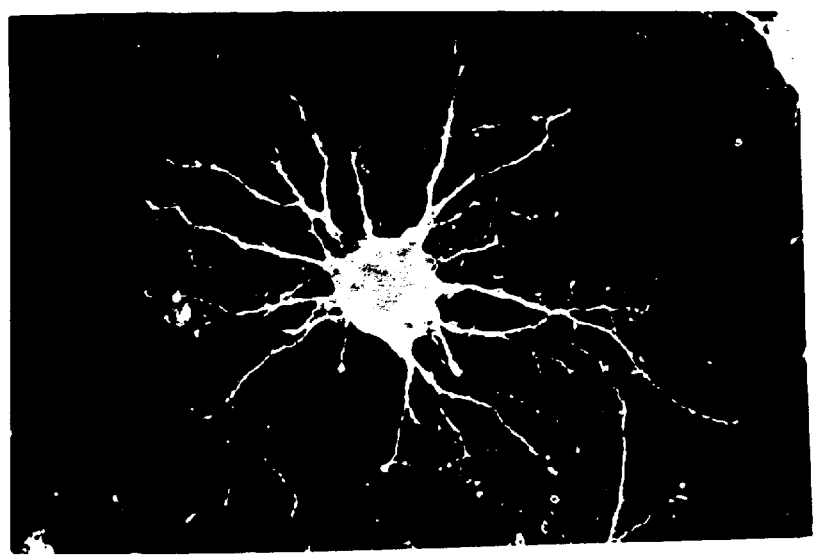

In the presence of anti-KAL Fab bound to the KAL-expressing cell monolayers, granule cell aggregates showed long and defasciculated neurites (FIGS. 8C, E). Some long neurites were induced to grow circumferentially instead of radially (FIG. 8C). The presence of pre-immune Fab had no effect on the fasciculation and growth inhibition of neurites observed on KAL-expressing CHO cells.

REFERENCES

Ballabio.

Bruce, H. M. (1959). An exteroceptive block to pregnancy in the mouse. Nature 184, 105.

BrÿmmendorÿF, T., and Rathjen, F. G. (1993). Axonal glycoproteins with immunoglobulin-and fibronectin type III related domains in vertebrates: structural features, binding activities, and signal transduction. J. Neurochem. 61, 1207–1219.

Brummendorf, T. Wolff, J. M., Frank, R., and Rathjen, F. G. (1989). Neural cell recognition molecule F11:homology with fibroectin type III and immunoglobulin type C domains. Neuron 2, 1351–61.

Burgoon, M. P., Grumer, M., Mauro, V., Edelman, G. M., and Cunningham, B. A. (1991). Structure of the chicken nuron-glia cell adhesion molecule, Ng-CAM: origin of the polypeptides and relation to the Ig superfamily, J. Cell. Biol. 112, 1017–29.

Dandekar, A. M., Robinson, E. A., Appella, E., and Qasba, P. K. 91982). Complete sequene analysis of cDNA clones encoding rat whey phosphoprotien: homology to a protease inhibitor. Proc. Natl. Acad. Sci. USA 79, 3987–3991.

De Morsier, G. (1954). Etudes sur les dysraphies cr%nio-enc phaliques. Schweiz Arch. Neurol. psychiat. 74, 309–361.

del Castillo, I., Cohen-Salmon, M., Blanchard, S., Lutfalla, G., and petit, C. (1992). Structure of the X-linked Kallmann syndrome gene and its homologous pseudogene on the Y chromosome. Nature Genet. 2, 305–310.

Edelman, G. M., and Crossin, K. L. (1991). Cell adhesion molecules: implications for a molecular histology. Annu. Rev. Biochem. 60, 155–190.

Engel, J. (1991). Common structural motifs in proteins of the extracellular matrix. Curr. Opinion in Cell Biol. 3, 779–785.

Branco, B., Guioli, S., Pragliola, A., incerti, B., Bardoni, B., Tonlorenzi, R., Carrozzo, R., Maestrini, E. Pieretti, M., Taillon-Miler, P., Brown, C. J., Willard H. Fr., lawrence, C., Persico, M. G., Camerino, G., and Ballaio, A. (1991). A gene deleted in Kallmann's syndrome shares homology with neural cell adhesion and axonal path-finding molecules. Nature 353, 529–536.

Furley, A. J., Morton, S. B., Manalo, D., Karagogeos, D., Dodd, J., and Jessell, T. M. (1990). THe axonal glycoprotein TAG-1 is an immunoglobulin superfamily member wtih neuite outgrowth-promoting activity. Cell 61, 157–70.

Gao, W. Q., Zheng, J. L., and Karihaleo, M. (1995). Neurotrophin-4/5 9NT-4/5) and brain-derived neurotrophic factor (BDNF0 act at later stages of cerebellar granule cell differentiation. J. Neurosci 15, 2656–67.

Gennarini, G., Cibelli, G., Rougon, G., Mattei, M. G., and Goridis, C. (1989). The mouse neuronal cell surface protein F3: a phosphatidylinositol-anchored member of the immunoglobulin superfamily related to chicken contactin. J. Cell. Biol. 109, 775–88.

Gotz, B., Scholze, A., Clement, A., Joester, A., Schutte, K., Wigger, F., Frank R., Spiess, E., Ekblom, P., and Faissner, A. (1996). Tenascin-C contains distinct adhesive, anti-adhesive, and neurite outgrowth promoting sites for neurons. j. Cell. Biol. 132, 681–99.

Greene, L. A., and Tischler, A. S. 91976), Establishment of a noradrenergic clonal line of rat adrenal pheochromocytoma cells which respond to nerve growth factor. proc. Natl Acad Sci USA 73, 2424–8.

Grumet, M., Mauro, V., Burgoon, M. P., Edelman, G. M., and Cunningham, B. A. (1991). Structure of a new nervous system glycoprotein, Nr-CAM, and its relationship to subgroups of neural cell adhesion molecules. J. Cell. Biol. 113, 1399–412.

Hardelin, J.-P., Levilliers, J., del Castillo, I., Cohen-Salmon, M., Legouis, R., Blanchard, S., Compain, S., Bouloux, P., Kirk, J., Moraine, C., Chaussain, J.-L., Weissenbach, J., and Petit, C. (1992). X chromosome-linked Kallmann syndrome: Stop mutations validate the candidate gene. Proc. Natl. Acad. Sci. USA 89, 8190–8194.

Hardelin, J.-P., and Petit, C. (1995). A molecular approach to the pathophysiology of the X chromoxome-linked kallmann's syndrome. In Genetic and Molecular Biological Aspects of Endocrine Disease, R. V. Thakker, ed. (London: Bailli re Tindall), pp. 489–507.

Hennighausen, L. G., and Sippel, A. E. (1982). Mouse whey acidic protein is a novel member of the family of 'four-disulfide core" proteins. Nucl. Acids Res. 10, 2677–2684.

Kallmann, F. J., Schoenfeld, W. A., and Barrera, S. E. (1944). The genetic aspects of primary eunochoidism. Am. J. Mental Deficiency XLVIII, 203–236.

Kato, I., and Tominaga, N. (1979). Trypsin-subtilisin inhibitor from red sea turtel eggwhite consits of two tandem domains, one KYnitz, one of a new family. Fed. Proc. 38, 832 9abstract).

Kayyem, J. F., Roman, J. M., de la Rosa, E. J., Schwarz, U., and Dreyer, W. J. (1992). Bravo/Nr-CAM is closely related to the cell adhesion molecules Li and Ng-CAM and has a similar heterodimer structure. J. Cell Biol. 118, 1259–70.

Legouis, R., Cohen-Salmon, M., del Castillo, I., Levilliers, J., Capy, L., Mornon, J.- P., and Petit, C. (1993). characterization of the chicken and quail homologues of the human gene responsible for the X-linked Kallmann syndrome. Genomics 17, 516–518.

Legouis, R., Hardelin, J.-P., Levilliers, J., Claverie, J.-M., Compain, S., Wunderle, V., Millasseau, P., Le Paslier, D., Cohert, D., Caterina, D., Bougueleret, L., Delemarre-Van de Waal, H., Lutfalla, G., Weissenbach, J., and Petit, C. (1991). The candidate gene for the X-linked Kallmann syndrome encodes a protein related to adhesion molecules. Cell 67, 423–435.

Legouis, R., Hardelin, J.-P., Petit, C., and Ayer-Le Li vre, C. (1994). Early expression of the KAL gene during emmbryonic development of the chick. Anat. Embryol. 190, 549–562.

McClintock, M. (1971). Menstrual synchrony and suppression. Nature 229, 244.

Moos, M., Tacke, R., Scherer, H., Teplow, D., Fruh, K., and Schachner, M. (1988). Neural adhesion molecule L1 as a member of the immunoglobulin superfamily with binding domains similir to fironectin. nature 334, 701–3.

Murakami (1994).

Murakami, S., Kukuyama, S., and Arai, Y. (1992). The origin of theluteinizing hormone-releasing hormone (LHRH) neurons in newts (Cynops pyrrhogaster): the effect of olfactory placode ablation. Cell Tussue Res. 269, 21–27.

Murakami, S., Seki, T., Wakabayashi, K., and Arai, Y. (1991). The ontogeny of luteinizing hormone-releasing hormone (LHRH) producing neurons int he chick embroyo: possible evidence for migrating LHRH neutrons from the olfactory epithelium expressing a highly polysialyated neural cell adhesion molecule. Neurosci. Res. 12, 421–431.

Naftolin, F., Harris, G. W., and Bobsow, M. (1971). Effect of purified luteinizing hormone releasing factor of normal and hypogonadotropic anosmic men. nature 232, 496–97.

Norenberg, U., Hubert, M., Brummendorf, T., Tarnok, A., and Rathjen, F. G. (1995). Characterization of functional domains of the tenascin-R (restrictin) polypeptide: cell attachment site, binding with F11, and enhancement of F11-mediated neurite outgrowth by tenascin-R. J. Cell. Biol. 130, 473–84.

Norgren (1991).

Ronnekleiv, O. K., and Resko, J. A. (1990). Ontogeny of gonadotropin-releasing hormone-containing neurons in early fetal development of Rhesus macaques: Endocrinology 126, 498–511.

Rugarli, E. I., Lutz, B., Kuratani, S. C., Wawersik, S., Borsani, G., Ballabio, A., and Eichele, G. (1993). Expression pattern of the Kallmann syndrome gene in the olfactory system suggests a role in neuronal targeting. Nature Genet. 4, 19–26.

Schwanzel-Fukuda, M., Abrahams, S., Crossin, K. L., Edelman, G. M., and Pfaff, D. W. (1992). Immunocytochemicall demonstration of neural cell adhesion molecule (NCAM) along the migration route of lateinizing hormone-releasing hormone (LHRH) neurons in mice. J. Comp. Neurol. 321, 1–18.

Schwanzel-Fukuda, M., Bick, D., and Pfaff, D. W. (1989). Luteinizing hormone-releasing hormone (LHRH)-expressing cells do not migrate normally in an inherited hypogonadal (Kallmann) syndrome. Mol. Brain Res. 6, 311–326.

Schwanzel-fukuda, M., and Pfaff, D. W. (1989). Origin of lutinizing hormone-releasing hormone neurons. Nature 338, 161–164.

Schwanzel-fukuda, M., and Pfaff, D. W. (1995). The structure and function of the nervus terminalis. In The handbook of clinical olfaction and teast, R. L. Doty, ed. 9new York: Dekker), pp. 835–864

SeemŸller, U., Arnhold, M., Fritz, H., Wiedenmann, K., Machleidt, W., Heinzel, R., Appelhans, H., Gassen, H.-G., and Lottspeich, F. (1986). The acid-stable proteinase inhibitor of human mucous secretions (HUSI-I, antileukoprotease). FEBS Lett. 199, 43–48.

Sherins, R. J., and Howards, S. S. (1986). Male infertility. In Campbell's Urology., P. C. Walsh, ed. (Philadelphia: Saunders, W. B.), pp. 640–697.

Sonderegger, P., and Rathjen, F. G. (1992). REgulation of axonal growth in the vertebrate nervous system by interactions between glycoproteins belonging to two subgroups of the immunoglobulin superfamily. J. Cell Biol. 119, 1387–1394.

Soussi-Y (1996). J. Cell. Sci.

Stetler, G., Brewer, M. T., and Thompson, R. C. (1986). Isolation and sequence of a human gene encoding a potent inhibitor of leucocyte proteases. Nucl. Acids Res. 14, 7883–7896.

Whitten, W. K. (1956). Modification of the oestrous cycle of the mouse by external stimuli associated with the male. J. Endoer. 13, 399, 404.

Wiedow, O., Schroder, J. M., Gregory, H., young, J. A., and Christophers, E. (1990). Elafin: an elastase-specific inhibitor of human skin. Purification, characterization, and complete amino acid sequence. j. Biol. Chem. 265, 14791–14795.

Wray, S., Grant, P., and Gainer, H. (1989). Evidence that cells expressing luteinizing hormone-releasing hormone mRNA in the mouse are derived from progenitor cells in the olfactory placode. proc. Natl. Acad. Sci. USA 86, 8132–8136.

Zuellig, R. A., Rader, C., Schroeder, A., Kalousek, M. B., Von Bohlen and Halbach, F., osterwalder, T., Inan, C., Stoeckli, E. T., Affolter, H. U., Fritz, A., and et al. (1992). Teh axonally secreted cell adhesion molecular axonin-1. Primary structure, immunoglobulin-like and fibronectin-type-III-like domains and glycosylphosphatidylinositol anchorage. Eur. J. Biochem. 204, 453–463.

What is claimed as new and is desired to be secured by Letters Patent of the United States is:

1. A composition comprising:
    a pharmaceutically acceptable carrier and
    an isolated fragment of KAL protein (SEQ ID NO: 1), wherein said fragment promotes the survival of neurons, promotes neurite outgrowth, or induces neurite fasciculation.

2. The composition of claim 1, wherein said KAL protein is selected from the group consisting of:
    a KAL fragment consisting of the sequence:
    beginning at position 182 and ending at position 286 of SEQ ID NO:1,
    beginning at position 287 and ending at position 403 of SEQ ID NO: 1,
    beginning at position 404 and ending at position 541 of SEQ ID NO: 1, and
    beginning at position 542 and ending at position 662 of SEQ ID NO: 1,
    or a portion of one of these fragments that promotes neuron survival, promotes neurite outgrowth, or promotes neurite fasciculation.

3. A method for promoting neuron survival comprising contacting a neuron with an effective amount of the composition of claim 1.

4. A method for promoting neurite outgrowth comprising contacting a neuron with an effective amount of the composition of claim 1.

5. A method for promoting neurite fasciculation comprising contacting a neuron with an effective amount of the composition of claim 1.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 680 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Met Val Pro Gly Val Pro Gly Ala Val Leu Thr Leu Cys Leu Trp Leu
1               5                   10                  15

Ala Ala Ser Ser Gly Cys Leu Ala Ala Gly Pro Gly Ala Ala Ala Ala
            20                  25                  30

Arg Arg Leu Asp Glu Ser Leu Ser Ala Gly Ser Val Gln Arg Ala Pro
            35                  40                  45

Cys Ala Ser Arg Cys Leu Ser Leu Gln Ile Thr Arg Ile Ser Ala Phe
50                  55                  60

Phe Gln His Phe Gln Asn Asn Gly Ser Leu Val Trp Cys Gln Asn His
65                  70                  75                  80

Lys Gln Cys Ser Lys Cys Leu Glu Pro Cys Lys Glu Ser Gly Asp Leu
            85                  90                  95

Arg Lys His Gln Cys Gln Ser Phe Cys Glu Pro Leu Phe Pro Lys Lys
                100                 105                 110

Ser Tyr Glu Cys Leu Thr Ser Cys Glu Phe Leu Lys Tyr Ile Leu Leu
            115                 120                 125

Val Lys Gln Gly Asp Cys Pro Ala Pro Glu Lys Ala Ser Gly Phe Ala
            130                 135                 140

Ala Ala Cys Val Glu Ser Cys Glu Val Asp Asn Glu Cys Ser Gly Val
145                 150                 155                 160

Lys Lys Cys Cys Ser Asn Gly Cys Gly His Thr Cys Gln Val Pro Lys
                165                 170                 175

Thr Leu Tyr Lys Gly Val Pro Leu Lys Pro Arg Lys Glu Leu Arg Phe
            180                 185                 190

Thr Glu Leu Gln Ser Gly Gln Leu Glu Val Lys Trp Ser Ser Lys Phe
            195                 200                 205

Asn Ile Ser Ile Glu Pro Val Ile Tyr Val Val Gln Arg Arg Trp Asn
            210                 215                 220

Tyr Gly Ile His Pro Ser Glu Asp Asp Ala Thr His Trp Gln Thr Val
225                 230                 235                 240
```

```
Ala Gln Thr Thr Asp Glu Arg Val Gln Leu Thr Asp Ile Arg Pro Ser
            245                 250                 255

Arg Trp Tyr Gln Phe Arg Val Ala Ala Val Asn Val His Gly Thr Arg
            260                 265                 270

Gly Phe Thr Ala Pro Ser Lys His Phe Arg Ser Ser Lys Asp Phe Ser
            275                 280                 285

Ala Pro Pro Ala Pro Ala Asn Leu Arg Leu Ala Asn Ser Thr Val Asn
            290                 295                 300

Ser Asp Gly Ser Val Thr Val Thr Ile Val Trp Asp Leu Pro Glu Glu
305                 310                 315                 320

Pro Asp Ile Phe Val His His Tyr Lys Val Phe Trp Ser Trp Met Val
                325                 330                 335

Ser Ser Lys Ser Leu Val Pro Thr Lys Lys Arg Arg Lys Thr Thr
            340                 345                 350

Asp Gly Phe Gln Asn Ser Val Ile Leu Glu Lys Leu Gln Pro Asp Cys
            355                 360                 365

Asp Tyr Val Val Glu Leu Gln Ala Ile Thr Tyr Trp Gly Gln Thr Arg
            370                 375                 380

Leu Lys Ser Ala Lys Val Ser Leu His Phe Thr Ser Thr His Ala Thr
385                 390                 395                 400

Asn Asn Lys Glu Gln Leu Val Lys Thr Arg Lys Gly Gly Ile Gln Thr
            405                 410                 415

Gln Leu Pro Phe Gln Arg Arg Pro Thr Arg Pro Leu Glu Val Gly
            420                 425                 430

Ala Pro Phe Tyr Gln Asp Gly Gln Leu Gln Val Lys Val Tyr Trp Lys
            435                 440                 445

Lys Thr Glu Asp Phe Thr Val Asn Arg Tyr His Val Arg Trp Phe Pro
            450                 455                 460

Glu Ala Cys Ala His Asn Arg Thr Thr Gly Ser Glu Ala Ser Ser Gly
465                 470                 475                 480

Met Thr His Glu Asn Tyr Ile Ile Leu Gln Asp Leu Ser Phe Ser Cys
            485                 490                 495

Lys Tyr Lys Val Thr Val Gln Pro Ile Arg Pro Lys Ser His Ser Lys
            500                 505                 510

Ala Glu Ala Val Phe Phe Thr Thr Pro Pro Cys Ser Ala Leu Lys Gly
            515                 520                 525

Lys Ser His Lys Pro Ile Gly Cys Leu Gly Glu Ala Gly His Val Leu
            530                 535                 540

Ser Lys Val Leu Ala Lys Pro Glu Asn Leu Ser Ala Ser Phe Ile Val
545                 550                 555                 560

Gln Asp Val Asn Ile Thr Gly His Phe Ser Trp Lys Met Ala Lys Ala
                565                 570                 575

Asn Leu Tyr Gln Pro Met Thr Gly Phe Gln Val Thr Trp Ala Glu Val
            580                 585                 590

Thr Thr Glu Ser Arg Gln Asn Ser Leu Pro Asn Ser Ile Ile Ser Gln
            595                 600                 605

Ser Gln Ile Leu Pro Ser Asp His Tyr Val Leu Thr Val Pro Asn Leu
            610                 615                 620

Arg Pro Ser Thr Leu Tyr Arg Leu Glu Val Gln Val Leu Thr Pro Gln
625                 630                 635                 640

Gly Glu Gly Pro Ala Thr Ile Lys Thr Phe Arg Thr Pro Glu Leu Pro
            645                 650                 655

Pro Ser Ser Ala His Arg Ser His Leu Lys His Arg Ala Pro His His
```

-continued

```
                    660                 665                 670
Tyr Lys Pro Ser Pro Glu Arg Tyr
        675                 680

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "SYNTHETIC DNA"

(xi) SEQUENCE DESCRIPTION: SEQ ID NO: 2:

CAGCCAATGG TGCGGCCTCC TGTC                                                    24

(2) INFORMATION FOR SEQ ID NO: 3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "SYNTHETIC DNA"

(xi) SEQUENCE DESCRIPTION: SEQ ID NO: 3:

TCCCGGCAGA CAGCGACTCC GT                                                      22
```